(12) United States Patent
Monani et al.

(10) Patent No.: US 11,801,284 B2
(45) Date of Patent: Oct. 31, 2023

(54) COMPOSITIONS AND METHODS FOR TREATING MOTOR NEURON DISEASES

(71) Applicant: The Trustees of Columbia University in the City of New York, New York, NY (US)

(72) Inventors: Umrao Monani, Oradell, NJ (US); Jeong Ki-Kim, Fort Lee, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 411 days.

(21) Appl. No.: 16/765,914

(22) PCT Filed: Dec. 13, 2018

(86) PCT No.: PCT/US2018/065469
§ 371 (c)(1),
(2) Date: May 21, 2020

(87) PCT Pub. No.: WO2019/118734
PCT Pub. Date: Jun. 20, 2019

(65) Prior Publication Data
US 2020/0360472 A1 Nov. 19, 2020

Related U.S. Application Data

(60) Provisional application No. 62/598,093, filed on Dec. 13, 2017.

(51) Int. Cl.
*A61K 38/17* (2006.01)
*A61K 35/761* (2015.01)
(Continued)

(52) U.S. Cl.
CPC ........ *A61K 38/1709* (2013.01); *A61K 9/0019* (2013.01); *A61K 9/0085* (2013.01);
(Continued)

(58) Field of Classification Search
CPC .... A61K 31/713; A61K 48/00; C12N 15/113; A61P 21/00
See application file for complete search history.

(56) References Cited

U.S. PATENT DOCUMENTS

| 7,226,748 B2 | 6/2007 | Georges et al. |
| 2009/0075948 A1 | 3/2009 | Parker |

(Continued)

FOREIGN PATENT DOCUMENTS

| EP | 3205647 A2 | 8/2017 |
| WO | 2014/026372 A1 | 2/2014 |
| WO | 2017/098467 A1 | 6/2017 |

OTHER PUBLICATIONS

Uytterhoeven et al. (Neuron, 2015 vol. 88:735-748).*
(Continued)

*Primary Examiner* — Terra C Gibbs
(74) *Attorney, Agent, or Firm* — Leason Ellis LLP

(57) ABSTRACT

The present disclosure provides compositions and methods of treating motor neuron diseases, including spinal muscular atrophy (SMA) and amyotrophic lateral sclerosis (ALS). A modulator of a heat shock protein, such as an Hsp70 family member protein, may be used in the present method. Alternatively, a mutant heat shock protein may be used.

14 Claims, 9 Drawing Sheets

(51) Int. Cl.
| | |
|---|---|
| A61K 38/46 | (2006.01) |
| A61P 21/00 | (2006.01) |
| C12N 15/113 | (2010.01) |
| A61K 9/00 | (2006.01) |
| A61K 48/00 | (2006.01) |

(52) U.S. Cl.
CPC .......... *A61K 35/761* (2013.01); *A61K 38/465* (2013.01); *A61P 21/00* (2018.01); *C12N 15/113* (2013.01); *A61K 48/00* (2013.01); *C12N 2310/11* (2013.01); *C12N 2310/14* (2013.01)

(56) References Cited

U.S. PATENT DOCUMENTS

| | | |
|---|---|---|
| 2015/0004151 A1 | 1/2015 | Jensen et al. |
| 2017/0165265 A1 | 6/2017 | Chiosis et al. |

OTHER PUBLICATIONS

Fernández-Fernández et al. (FEBS Letters, 2017 vol. 591:2648-2660).*
Turturici et al. (Biochemistry Research International, 2011 vol. 2011:1-18).*
Molecular Chaperones and Folding Catalysts, Edited by Bernd Bukau (Apr. 21, 2014, Chapter 25).*
Mastermind, HSPA8 gene, downloaded from https://mastermind.genomenon.com/detail?gene=hspa8&mutation=hspa8:A30C&disease=all%20diseases&boolean=true&gene_op=and&mutation_op=and&cnv_op=and&disease_op=and&hpo_op=and&unii_op= and &keyword_op=and EASES / HSPA8:A30C Articles in Mastermind (genomenon.com) on Dec. 12, 2022.*
Houenou et al., Exogenous Heat Shock Cognate Protein Hsc70 Prevents Axotomy-Induced Death of Spinal Sensory Neurons, Cell stress & Chaperones, 1996, vol. 1, No. 3, pp. 161-166.
Coyne et al., Post-Transcriptional Inhibition of Hsc70-4/HSPA8 Expression Leads to Synaptic Vesicle Cycling Defects In Multiple Models of ALS, Cell reports, 2017, vol. 21, No. 1, pp. 110-125.
International Search Report and Written Opinion of corresponding international application PCT/US18/65469, dated Feb. 26, 2019.
Orrell RW. "Motor neuron disease: systematic reviews of treatment for ALS and SMA", Br Med Bull. 2010; 93: pp. 145-159.
Gama-Carvalho et al. "Linking amyotrophic lateral sclerosis and spinal muscular atrophy through RNA-transcriptome homeostasis: a genomics perspective", J Neurochem. 2017, 141(1): pp. 12-30.
Loeffler DA. et al. "Age-related decrease in heat shock 70-kDa protein 8 in cerebrospinal fluid is associated with increased oxidative stress": Frontiers in Aging Neuroscience, 2016, vol. 8, Article 178.
Cristofani R et al."Inhibition of retrograde transport modulates misfolded protein accumulation and clearance in motoneuron diseases", Autophagy, 2017, vol. 13, Issue 8, pp. 1280-1303.
Tsuiji H. et al. "Spliceosome integrity is defective in the motor neuron diseases ALS and SMA", EMBO Molecular Medicine, 2013, vol. 5, Issue 2, pp. 221-234.
Cirulli ET et al. "Exome sequencing in amyotrophic lateral sclerosis identifies risk genes and pathways", Science, 2015 vol. 347, Issue 6229, pp. 1436-1441.
NIH Grant#: 4R01NS057482-09. Monani U, "Novel genetic determinants of the neuromuscular SMA phenotype". Budget Start Date: Jun. 1, 2016. Budget End Date: May 31, 2018.
Sahu et al. (Jan. 2011) Microautophagy of cytosolic proteins by late endosomes. Dev Cell. 20:131-9.
Lee et al. (Sep. 2012) Limited phenotypic effects of selectively augmenting the SMN protein in the neurons of a mouse model of severe spinal muscular atrophy. PLoS One. 7:e46353.
Gogliotti et al. (Mar. 2012) Motor neuron rescue in spinal muscular atrophy mice demonstrates that sensory-motor defects are a consequence, not a cause, of motor neuron dysfunction. J Neurosci. 32:3818-29.

Guettier-Sigrist et al. (Mar. 2002) Possible pathogenic role of muscle cell dysfunction in motor neuron death in spinal muscular atrophy. Muscle Nerve. 25:700-8.
Shafey et al. (Oct. 2005) Hypomorphic Smn knockdown C2C12 myoblasts reveal intrinsic defects in myoblast fusion and myotube morphology. Exp Cell Res. 311:49-61.
Kanisicak et al. (Aug. 2009) Progenitors of skeletal muscle satellite cells express the muscle determination gene, MyoD. Dev Biol. 332:131-41.
Montes, et al. (2011) Six-Minute Walk Test demonstrates motor fatigue in spinal muscular atrophy. Neurology 74:833-838; Mar. 2010.
Tang et al. (Jan. 2017) Brain microvasculature defects and Glut1 deficiency syndrome averted by early repletion of the glucose transporter-1 protein. Nat Commun. 8:14152.
Rudnicki et al. (2008) The molecular regulation of muscle stem cell function. Cold Spring Harb Symp Quant Biol 10.1101/sqb.2008.73.064.
Swoboda et al. (May 2005) Natural history of denervation in SMA: relation to age, SMN2 copy number and function. Ann Neurol. 57:704-12.
Lutz et al. (Aug. 2011) Postsymptomatic restoration of SMN rescues the disease phenotype in a mouse model of severe spinal muscular atrophy. J Clin Invest. 12:3029-41.
Hua et al. (2013) Peripheral SMN restoration is essential for long-term rescue of a severe spinal muscular atrophy mouse model. Nature 478: 123-6. Published online Oct. 2011.
Hosseinibarkooie S et al (Sep. 2016) The Power of Human Protective Modifiers: PLS3 and CORO1C Unravel Impaired Endocytosis in Spinal Muscular Atrophy and Rescue SMA Phenotype. Am J Hum Genet. 99:647-65.
Riessland, M et al. (Feb. 2017) Neurocalcin Delta Suppression Protects against Spinal Muscular Atrophy in Humans and across Species by Restoring Impaired Endocytosis. Am J Hum Genet. 100: 297-315.
Orrell RW, Motor neuron disease: systematic reviews of treatment for ALS and SMA, Br. Med. Bull. 2010; 93: 145-59.
Gama-Carvalho et al., Linking amyotrophic lateral sclerosis and spinal muscular atrophy through RNA-transcriptome homeostasis: a genomics perspective, J Neurochem. 2017, 141(1): 12-30.
Lefebvre et al., Identification and characterization of a spinal muscular atrophy-determining gene, Cell, (Jan. 1995) 80:155-65.
Lefebvre et al., Correlation between severity and SMN protein level in spinal muscular atrophy. Nat. Genet. (Jul. 1997) 16: 265-69.
Coovert et al., (Aug. 1997) The survival motor neuron protein in spinal muscular atrophy. Hum Mol Genet. 8:1205-14.
Rochette et al. (Mar. 2001) SMN gene duplication and the emergence of the SMN2 gene occurred in distinct hominids: SMN2 is unique to *Homo sapiens*. Hum Genet. 108:255-66.
Monani, UR (Dec. 2005) Spinal muscular atrophy: a deficiency in a ubiquitous protein; a motor neuron-specific disease. Neuron. 48:885-96.
Monani et al., (Jul. 1999) A single nucleotide difference that alters splicing patterns distinguishes the SMA gene SMN1 from the copy gene SMN2. Hum Mol Genet. 7:1177-83.
Lorson et al., (May 1999) A single nucleotide in the SMN gene regulates splicing and is responsible for spinal muscular atrophy. Proc Natl Acad Sci U S A. 96:6307-11.
Singh et al. (Feb. 2006) Splicing of a critical exon of human Survival Motor Neuron is regulated by a unique silencer element located in the last intron. Mol Cell Biol. 26:1333-46.
Hua et al. (Apr. 2007) Enhancement of SMN2 exon 7 inclusion by antisense oligonucleotides targeting the exon. PLoS Biol. 5:e73.
Hua et al. (Apr. 2008) Antisense masking of an hnRNP A1/A2 intronic splicing silencer corrects SMN2 splicing in transgenic mice. Am J Hum Genet. 82:834-48.
Porensky et al. (2012) A single administration of morpholino antisense oligomer rescues spinal muscular atrophy in mouse. Hum Mol Genet. 21:1625-1638.
D'Ydewalle et al. (Jan. 2015) Spinal Muscular Atrophy Therapeutics: Where do we Stand? Neurotherapeutics. 12:303-16.
Pellizzoni L (Apr. 2007) Chaperoning ribonucleoprotein biogenesis in health and disease. EMBO Rep. 8:340-5.

(56) References Cited

OTHER PUBLICATIONS

Chari et al. (Mar. 2009) The role of RNP biogenesis in spinal muscular atrophy. Curr Opin Cell Biol. 2:387-93.
Schrank et al. (Sep. 1997) Inactivation of the survival motor neuron gene, a candidate gene for human spinal muscular atrophy, leads to massive cell death in early mouse embryos. Proc Natl Acad Sci U S A. 94:9920-5.
Monani et al., Neurodegeneration in spinal muscular atrophy: from disease phenotype and animal models to therapeutic strategies and beyond.(Jan. 2014) Future Neurol. 9:49-65.
Cifuentes-Diaz et al. (Mar. 2001) Deletion of murine SMN exon 7 directed to skeletal muscle leads to severe muscular dystrophy. J Cell Biol. 152:1107-14.
Gavrilina et al. (Apr. 2008) Neuronal SMN expression corrects spinal muscular atrophy in severe SMA mice while muscle-specific SMN expression has no phenotypic effect. Hum Mol Genet. 17:1063-75.
Iyer et al. (Aug. 2015) Low levels of Survival Motor Neuron protein are sufficient for normal muscle function in the SMN$\Delta$7 mouse model of SMA. Hum Mol Genet. 24:6160-73.
Hayhurst et al. A cell-autonomous defect in skeletal muscle satellite cells expressing low levels of survival of motor neuron protein. (Aug. 2012) Dev Biol. 368:323-34.
Boyer et al. (2013) Early onset muscle weakness and disruption of muscle proteins in mouse models of spinal muscular atrophy. Skelet Muscle. 3:24.
Martinez et al. (Jun. 2012) Survival motor neuron protein in motor neurons determines synaptic integrity in spinal muscular atrophy. J Neurosci. 32:8703-15.
Buchner et al. (Aug. 2003) SCNM1, a putative RNA splicing factor that modifies disease severity in mice. Science. 30:967-9.
Nadeau JH (2003) Modifier genes and protective alleles in humans and mice. Curr Opin Genet Dev. 13:290-5.
Le et al. (Feb. 2005) SMNDelta7, the major product of the centromeric survival motor neuron (SMN2) gene, extends survival in mice with spinal muscular atrophy and associates with full-length SMN. Hum Mol Genet. 14:845-57.
Monani et al. (Feb. 2000) The human centromeric survival motor neuron gene (SMN2) rescues embryonic lethality in Smn(-/-) mice and results in a mouse with spinal muscular atrophy. Hum Mol Genet. 9:333-9.
Miniou et al. (Oct. 1999) Gene targeting restricted to mouse striated muscle lineage. Nucleic Acids Res. 27:e27.
Burghes et al. (Aug. 2009) Spinal muscular atrophy: why do low levels of survival motor neuron protein make motor neurons sick? Nat Rev Neurosci. 10:597-609.
Park et al. (Sep. 2010) Reduced survival of motor neuron (SMN) protein in motor neuronal progenitors functions cell autonomously to cause spinal muscular atrophy in model mice expressing the human centromeric (SMN2) gene. J Neurosci. 30:12005-19.
Ling et al. (Nov. 2010) Synaptic defects in the spinal and neuromuscular circuitry in a mouse model of spinal muscular atrophy. PLoS One 5:e15457.
Mentis et al. (Feb. 2011) Early functional impairment of sensory-motor connectivity in a mouse model of spinal muscular atrophy. Neuron. 69:453-67.
Kariya et al. (May 2008) Reduced SMN protein impairs maturation of the neuromuscular junctions in mouse models of spinal muscular atrophy. Hum Mol Genet. 17:2552-69.
Heiman-Patterson et al. (Jan. 2011) Effect of genetic background on phenotype variability in transgenic mouse models of amyotrophic lateral sclerosis: a window of opportunity in the search for genetic modifiers. Amyotroph Lateral Scler. 12:79-86.
Li et al. (Oct. 2015) $\alpha$-COP binding to the survival motor neuron protein SMN is required for neuronal process outgrowth. Hum Mol Genet. 24:7295-307.
Custer et al. (Oct. 2016) Altered mRNA Splicing in SMN-Depleted Motor Neuron-Like Cells. PLoS One. 11:e0163954.
Uytterhoeven et al. (Nov. 2015) Hsc70-4 Deforms Membranes to Promote Synaptic Protein Turnover by Endosomal Microautophagy. Neuron. 88:735-48.
Torres-Benito et al. (Oct. 2011) SMN requirement for synaptic vesicle, active zone and microtubule postnatal organization in motor nerve terminals. PLoS One. 6:e26164.
Kong et al. (Jan. 2009) Impaired synaptic vesicle release and immaturity of neuromuscular junctions in spinal muscular atrophy mice. J Neurosci. 29:842-51.
Lotti et al. (Oct. 2012) An SMN-dependent U12 splicing event essential for motor circuit function. Cell. 151:440-54.
Singh et al. (2015) A mouse geneticist's practical guide to CRISPR applications. Genetics. 199:1-15.
Butchbach et al. (Aug. 2007) Abnormal motor phenotype in the SMNDelta7 mouse model of spinal muscular atrophy. Neurobiol Dis. 27:207-19.
El-Khodor et al. (Mar. 2008) Identification of a battery of tests for drug candidate evaluation in the SMNDelta7 neonate model of spinal muscular atrophy. Exp Neurol. 212:29-43.
Meister et al. (Nov. 2001) A multiprotein complex mediates the ATP-dependent assembly of spliceosomal U snRNPs. Nat Cell Biol 3:945-9.
Elso et al. (2004) Leishmaniasis host response loci (lmr13) modify disease severity through a Th1/Th2-independent pathway. Genes Immunity 5:93-100.
Liu et al. (Dec. 2012) Comprehensive review on the HSC70 functions, interactions with related molecules and involvement in clinical diseases and therapeutic potential. Pharmacol Ther. 136:354-74.
McPherson P.S. (Nov. 2015) Eating Locally: Microautophagy and Protein Turnover at the Synapse. Neuron. 38:619-21.
Wilhelm et al. (May 2014) Composition of isolated synaptic boutons reveals the amounts of vesicle trafficking proteins. Science. 344:1023-8.
Huang et al. (Jan. 1993) Aspartyl residue 10 is essential for ATPase activity of rat hsc70. J Biol Chem. 268:2063-8.
Matta S et al. (Sep. 2012) LRRK2 controls an EndoA phosphorylation cycle in synaptic endocytosis. Neuron. 75:1008-21.
Shimazu et al. (Feb. 2005) A family of basic amino acid transporters of the vacuolar membrane from *Saccharomyces cerevisiae*. J Biol Chem. 280:4851-7.

\* cited by examiner

COMPOSITIONS AND METHODS FOR TREATING MOTOR NEURON DISEASES

CROSS REFERENCE TO RELATED APPLICATION

The present application claims priority to U.S. patent application No. 62/598,093, filed Dec. 13, 2017, which is hereby incorporated by reference in its entirety.

STATEMENT OF GOVERNMENT SUPPORT

This invention was made with government support under grant NS057482 awarded by the National Institutes of Health. The government has certain rights in the invention.

FIELD OF THE INVENTION

The present invention relates to compositions and methods for treating motor neuron diseases.

BACKGROUND

Two of the most common and deadly motor neuron diseases are spinal muscular atrophy (SMA), which primarily manifests in infancy, and amyotrophic lateral sclerosis (ALS), which generally manifests in adulthood. Both conditions carry a prognosis of 2-3 years, with few effective treatment options (Orrell R W, Motor neuron disease: systematic reviews of treatment for ALS and SMA, Br. Med. Bull. 2010; 93: 145-59). SMA mortality results from a degeneration of the spinal motor neurons and consequent paralysis of muscles that the neurons innervate.

Spinal muscular atrophy (SMA) is a severe, autosomal recessive, neuromuscular disorder and the most common inherited cause of infant mortality. SMA is caused by mutations in the Survival of Motor Neuron 1 (SMN1) gene and low levels of its translated product, the SMN protein[1-3]. In humans, most (~90%) of the SMN protein derives from SMN1; an almost identical paralogue, SMN2, expresses the rest but fails to prevent the onset of disease in individuals lacking SMN1. SMA is a uniquely human disease, stemming from the presence, in *H. sapiens* alone[4], of a copy gene, SMN2, which is invariably present in patients but unable to prevent disease onsets[5]. The inability of SMN2 to prevent disease is owed to a synonymous, exon 7 C→T nucleotide transition that alters the splicing pattern of the gene so that only minimal amounts of full-length (FL) SMN transcript and correspondingly low levels of functional protein are expressed from it[2, 3, 6, 7]. However, since the SMN2 splicing defect can be rectified in vitro[8, 9] as well as in vivo[10, 11], it has been the target of choice as a means to a treatment for SMA[12]. A splice-altering mutation within it that results in diminished levels of the full-length transcript and, consequently, low SMN protein, can be targeted to restore SMN levels. This strategy has been vigorously pursued as a means to a treatment for SMA, recently culminating in FDA approval of Spinraza®, a SMN-inducing antisense oligonucleotide (ASO) drug. However, explanations for how SMN maintains the health and viability of the neuromuscular system and why depletion of the protein triggers selective motor neuron (MN) death remain elusive.

The SMN protein is ubiquitously expressed and best known for its essential role in orchestrating the splicing cascade[13, 14]; complete loss of protein is lethal[15]. Yet, low levels such as those seen in SMA have a decidedly selective effect, triggering spinal MN loss and neuromuscular dysfunction[16]. In most patients, other organ systems remain relatively unaffected. This lack of congruence between the housekeeping function of the SMN protein and the selective vulnerability of the nerve-muscle axis to protein depletion has remained the single most puzzling aspect of the disease. There is still no consensus on whether low SMN in muscle is truly deleterious and if restoring protein to this tissue will yield any additional benefit to that observed following CNS-specific repletion[17-22]. Studies indicate that the SMN protein also plays a role in the pathogenesis of other motor neuron diseases such as amyotrophic lateral sclerosis (ALS).

Recent work has indicated there are genetic and etiological similarities between SMA and ALS, namely, a disruption of RNA processing appears to be involved in both. These findings open up the possibility of a common treatment strategy for SMA and ALS (Gama-Carvalho et al., Linking amyotrophic lateral sclerosis and spinal muscular atrophy through RNA-transcriptome homeostasis: a genomics perspective, J Neurochem. 2017, 141(1): 12-30). There is still a need to identify effective treatments for SMA, ALS and other motor neuron disorders.

SUMMARY

The present disclosure provides for a method of treating a motor neuron disease in a subject. The present disclosure provides for a method for treating a neurodegenerative disorder, as well as other conditions as described herein.

The method may comprise administering an effective amount of a nucleic acid molecule encoding a mutant Hsp70 family member protein (e.g., a mutant Hspa8) to the subject.

The method may comprise administering an effective amount of a mutant Hsp70 family member protein (e.g., a mutant Hspa8) to the subject.

The mutant Hsp70 family member protein (e.g., a mutant Hspa8) may comprise a missense mutation, such as $Hspa8^{G470R}$.

The mutant Hsp70 family member protein (e.g., a mutant Hspa8) may comprise a mutation in a substrate binding domain of the Hsp70 family member protein (e.g., Hspa8). The mutant Hsp70 family member protein (e.g., a mutant Hspa8) may comprise a mutation in an ATPase domain of the Hsp70 family member protein (e.g., Hspa8).

The mutant Hsp70 family member protein (e.g., a mutant Hspa8) may have a lower chaperone activity than the wildtype Hsp70 family member protein (e.g., wildtype Hspa8). The mutant Hsp70 family member protein (e.g., a mutant Hspa8) may have a greater microautophagy activity than the wildtype Hsp70 family member protein (e.g., wildtype Hspa8).

The method may comprise administering an effective amount of a modulator of a Hsp70 family member protein (e.g., Hspa8) to the subject.

The method may comprise administering an effective amount of a nucleic acid molecule encoding a modulator of a Hsp70 family member protein (e.g., Hspa8) to the subject.

The modulator may bind to a substrate binding domain of a Hsp70 family member protein (e.g., Hspa8). The modulator may bind to an ATPase domain of a Hsp70 family member protein (e.g., Hspa8).

The modulator may decrease a chaperone activity of a Hsp70 family member protein (e.g., Hspa8). The modulator may increase a microautophagy activity of a Hsp70 family member protein (e.g., Hspa8).

In one embodiment, the modulator is an inhibitor of a Hsp70 family member protein (e.g., Hspa8).

The modulator may be a small molecule, a polynucleotide (e.g., a small interfering RNA (siRNA) or an antisense molecule), or an antibody or antigen-binding portion thereof. The modulator may comprise a CRISPR/Cas system.

The modulator may be administered to the central nervous system (CNS) of the subject. The modulator may be administered to the spinal cord of the subject. The modulator may be administered by intrathecal injection. The modulator may be administered orally, intravenously, intramuscularly, topically, arterially, or subcutaneously.

The nucleic acid molecule may comprise a recombinant adeno-associated virus (AAV) vector, such as AAV9 or any other AAV as described herein.

The nucleic acid molecule may be administered to the central nervous system (CNS) of the subject. The nucleic acid molecule may be administered to the spinal cord of the subject. The nucleic acid molecule may be administered by intrathecal injection. The nucleic acid molecule may be administered orally, intravenously, intramuscularly, topically, arterially, or subcutaneously.

The method may further comprise administering a SMN2 splicing modifier to the subject.

The motor neuron disease may be spinal muscular atrophy (SMA) and/or amyotrophic lateral sclerosis (ALS). The motor neuron disease may be hereditary spastic paraplegia (HSP), primary lateral sclerosis (PLS), progressive muscular atrophy (PMA), progressive bulbar palsy (PBP), and/or pseudobulbar palsy.

The subject may be a mammal, such as a human, a rodent, or a simian.

BRIEF DESCRIPTION OF THE DRAWINGS

For the purpose of illustrating the invention, there are depicted in drawings certain embodiments of the invention. However, the invention is not limited to the precise arrangements and instrumentalities of the embodiments depicted in the drawings.

DETAILED DESCRIPTION OF THE INVENTION

Figure 1A:
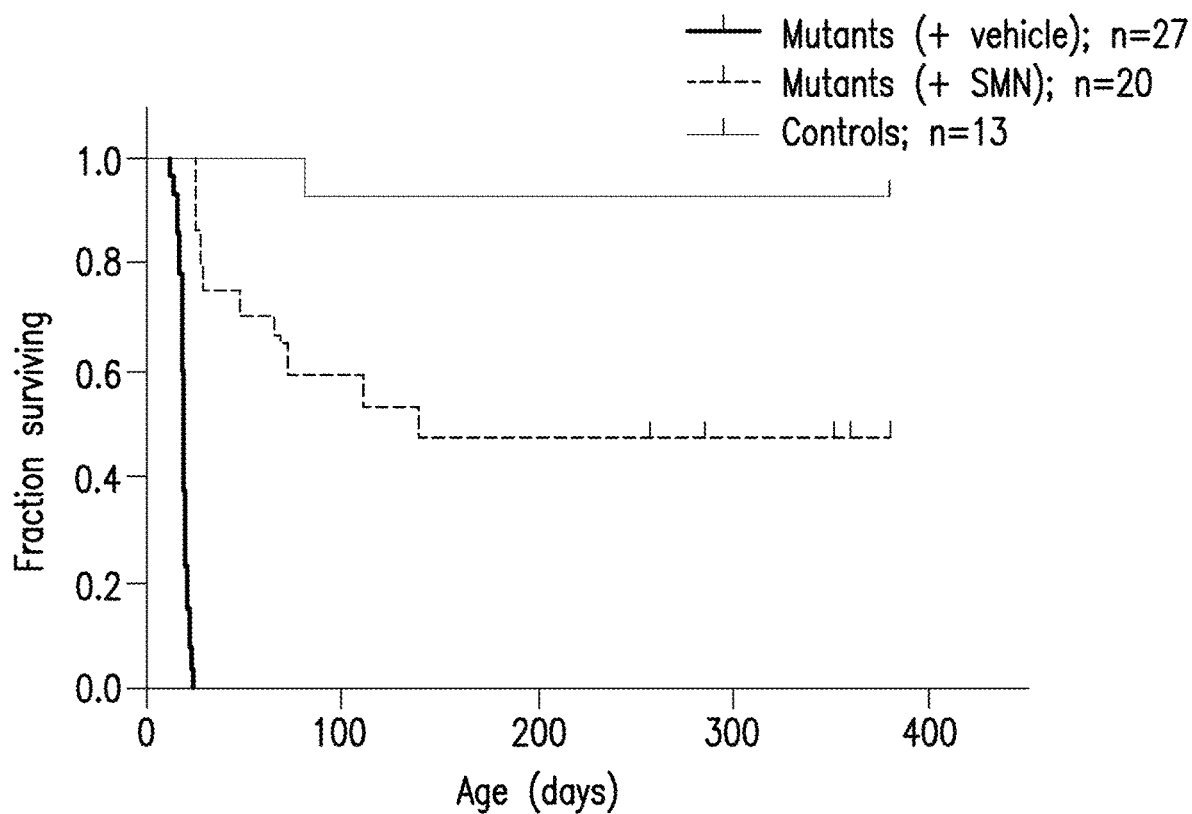
FIGS. 1A-1D. SMN repletion rescues the disease phenotype of SMA mice. Early postnatal restoration of the SMN protein (A) extends lifespan, (B) augments SMN in motor neurons; arrows depict nuclear SMN, (C) prevents neurodegeneration and (D) restores muscle strength as assessed in a grip strength assay.
Figure 1B:
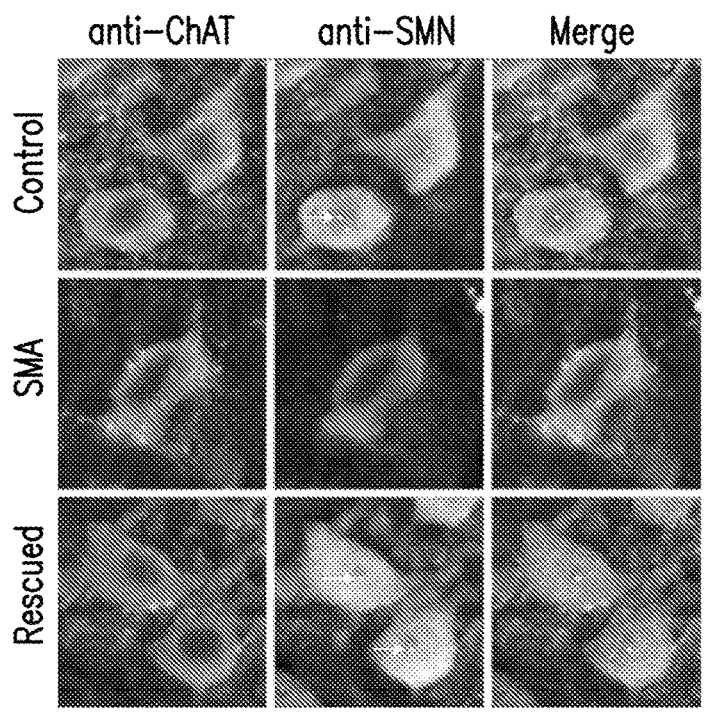
Figure 1C:
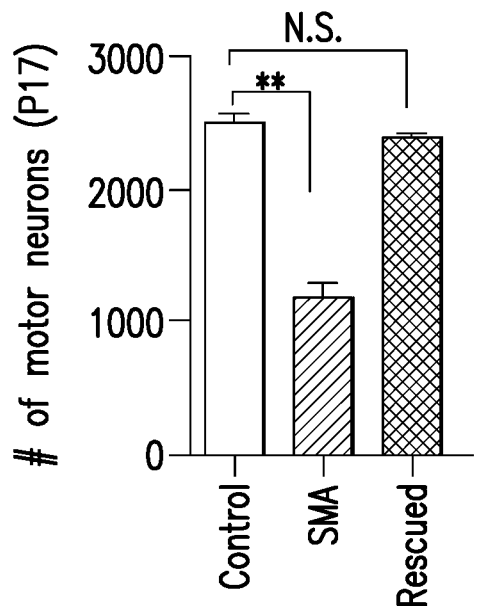
Figure 1D:
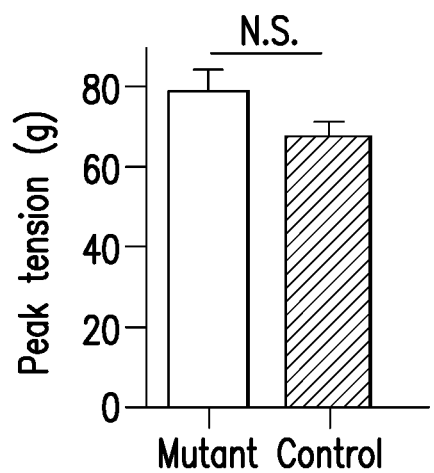

The present disclosure provides methods of treating motor neuron diseases, including spinal muscular atrophy (SMA) and amyotrophic lateral sclerosis (ALS). A modulator of a heat shock protein, such as an Hsp70 family member protein, may be used in the present method. Alternatively, a mutant heat shock protein/polypeptide may be used. The method may also serve as an adjunct therapy for a motor neuron disease, or may be used to treat patients who do not respond to an existing therapy (e.g., a SMN2 splicing modifier).

The Hsp70 family member proteins include, but are not limited to, Hspa8 (Hsp70-8, or Hsc70), Hsp70, Hsp70-2, Hsp70-4, Hsp70-4L, Hsp70-5, Hsp70-6, Hsp70-7, Hsp70-9, Hsp70-12a, and Hsp70-14.

The present method of treating a motor neuron disease in a subject may comprise administering an effective amount of a nucleic acid molecule encoding a mutant Hsp70 family member protein/polypeptide (e.g., Hspa8) to the subject. The present method may comprise administering an effective amount of a mutant Hsp70 family member protein/polypeptide (e.g., Hspa8) to the subject.

The mutant Hsp70 family member protein (e.g., Hspa8) may have a point mutation, a missense mutation, a nonsense mutation compared to the wildtype Hsp70 family member protein (e.g., Hspa8). The mutation may decrease/disrupt the chaperone activity of the protein (e.g., shifting the function of the protein toward microautophagy such as synaptic microautophagy). The mutation may be in the substrate binding domain of the heat shock protein. The mutation may be in the ATPase domain of the heat shock protein. In one embodiment, the mutant Hsp70 family member protein is Hspa8$^{G470R}$.

The mutant Hsp70 family member protein (e.g., Hspa8) may have a lower chaperone activity than the wildtype Hsp70 family member protein (e.g., Hspa8). The mutant Hsp70 family member protein (e.g., Hspa8) may have a greater microautophagy activity than the wildtype Hsp70 family member protein (e.g., Hspa8).

The nucleic acid molecule encoding the mutant Hsp70 family member protein (e.g., Hspa8) may comprise a viral vector, e.g., a recombinant adeno-associated virus (AAV) vector, encoding the mutant Hsp70 family member protein (e.g., Hspa8).

The present method of treating a motor neuron disease in a subject may comprise administering an effective amount of a modulator of a mutant Hsp70 family member protein/polypeptide (e.g., Hspa8) to the subject.

The present method of treating a motor neuron disease in a subject may comprise administering an effective amount of a nucleic acid molecule encoding a modulator of a mutant Hsp70 family member protein/polypeptide (e.g., Hspa8) to the subject.

In one embodiment, the modulator binds to a substrate binding domain of a Hsp70 family member protein (e.g., Hspa8). In another embodiment, the modulator binds to an ATPase domain of a Hsp70 family member protein (e.g., Hspa8).

The modulator may decrease a chaperone activity of a Hsp70 family member protein (e.g., Hspa8). The modulator may increase a microautophagy activity of a Hsp70 family member protein (e.g., Hspa8). In one embodiment, the modulator is an inhibitor of a Hsp70 family member protein (e.g., Hspa8).

The modulator may be a small molecule, a polynucleotide (e.g., a small interfering RNA (siRNA) or an antisense molecule), or an antibody or antigen-binding portion thereof. The modulator may comprise a CRISPR/Cas9 system.

The nucleic acid molecule encoding the modulator of a mutant Hsp70 family member protein/polypeptide (e.g., Hspa8) may comprise a viral vector, e.g., a recombinant adeno-associated virus (AAV) vector, encoding the modulator of a mutant Hsp70 family member protein/polypeptide (e.g., Hspa8).

The present composition and method may result in an increase in the autophagy (e.g., microautophagy) activity of a Hsp70 family member protein (e.g., Hspa8), where the autophagy (e.g., microautophagy) activity of a Hsp70 family member protein (e.g., Hspa8) affected by the present composition and method is (at least) about 2-fold, (at least) about 3-fold, (at least) about 4-fold, (at least) about 5-fold, (at least) about 6-fold, (at least) about 7-fold, (at least) about 8-fold, (at least) about 9-fold, (at least) about 10-fold, (at least) about 1.1-fold, (at least) about 1.2-fold, (at least) about 1.3-fold, (at least) about 1.4-fold, (at least) about 1.5-fold, (at least) about 1.6-fold, (at least) about 1.8-fold, at least 2-fold, at least 3-fold, at least 4-fold, at least 5-fold, at least 6-fold, at least 7-fold, at least 8-fold, at least 9-fold, at least 10-fold, (at least) about 15-fold, (at least) about 20-fold, (at least) about 50-fold, (at least) about 100-fold, (at least) about 120-fold, from about 2-fold to about 500-fold, from about 1.1-fold to about 10-fold, from about 1.1-fold to about 5-fold, from about 1.5-fold to about 5-fold, from about 2-fold to about 5-fold, from about 3-fold to about 4-fold, from about 5-fold to about 10-fold, from about 5-fold to about 200-fold, from about 10-fold to about 150-fold, from about 10-fold to about 20-fold, from about 20-fold to about 150-fold, from about 20-fold to about 50-fold, from about 30-fold to about 150-fold, from about 50-fold to about 100-fold, from about 70-fold to about-150 fold, from about 100-fold to about 150-fold, from about 10-fold to about 100-fold, from about 100-fold to about 200-fold, of the original autophagy (e.g., microautophagy) activity of a Hsp70 family member protein (e.g., Hspa8) (in the absence of the present composition and method).

The present composition and method may result in a decrease in the chaperone activity of a Hsp70 family member protein (e.g., Hspa8), where the chaperone activity of a Hsp70 family member protein (e.g., Hspa8) affected by the present composition and method is no greater than 90%, no greater than 85%, no greater than 80%, no greater than 75%, no greater than 70%, no greater than 65%, no greater than 60%, no greater than 55%, no greater than 50%, no greater than 45%, no greater than 40%, no greater than 35%, no greater than 30%, no greater than 25%, no greater than 20%, no greater than 15%, no greater than 10%, about 10% to about 90%, about 15% to about 80%, about 20% to about 70%, about 25% to about 60%, about 30% to about 50%, about 30% to about 40%, about 25% to about 40%, about 20% to about 30%, about 25% to about 35%, about 10% to about 30%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 20% to about 50%, about 12.5% to about 80%, about 20% to about 70%, about 25% to about 60%, or about 25% to about 50%, about 1% to about 100%, about 5% to about 90%, about 10% to about 80%, about 5% to about 70%, about 5% to about 60%, about 10% to about 50%, about 15% to about 40%, about 5% to about 20%, about 1% to about 20%, about 10% to about 30%, about 5% to about 10%, about 20%, about 30%, about 40%, about 50%, about 60%, about 70%, about 80%, about 90%, about 100%, about 10% to about 90%, about 12.5% to about 80%, about 20% to about 70%, about 25% to about 60%, or about 25% to about 50%, of the original chaperone activity of a Hsp70 family member protein (e.g., Hspa8) (in the absence of the present composition and method).

The present composition and method may result in an increase in motor neuron number, neuromuscular junction (NMJ) electrophysiology (e.g., miniature end-plate potentials (mEPPs), end-plate potentials (EPPs), Quantal content), neurotransmission at the NMJ, muscle strength, etc. of the subject, where the motor neuron number, neuromuscular junction (NMJ) electrophysiology (e.g., miniature end-plate potentials (mEPPs), end-plate potentials (EPPs), Quantal content), neurotransmission at the NMJ, muscle strength, etc. of the subject affected by the present composition and method is (at least) about 2-fold, (at least) about 3-fold, (at least) about 4-fold, (at least) about 5-fold, (at least) about 6-fold, (at least) about 7-fold, (at least) about 8-fold, (at least) about 9-fold, (at least) about 10-fold, (at least) about 1.1-fold, (at least) about 1.2-fold, (at least) about 1.3-fold, (at least) about 1.4-fold, (at least) about 1.5-fold, (at least) about 1.6-fold, (at least) about 1.8-fold, at least 2-fold, at least 3-fold, at least 4-fold, at least 5-fold, at least 6-fold, at least 7-fold, at least 8-fold, at least 9-fold, at least 10-fold, (at least) about 15-fold, (at least) about 20-fold, (at least) about 50-fold, (at least) about 100-fold, (at least) about 120-fold, from about 2-fold to about 500-fold, from about 1.1-fold to about 10-fold, from about 1.1-fold to about 5-fold, from about 1.5-fold to about 5-fold, from about 2-fold to about 5-fold, from about 3-fold to about 4-fold, from about 5-fold to about 10-fold, from about 5-fold to about 200-fold, from about 10-fold to about 150-fold, from about 10-fold to about 20-fold, from about 20-fold to about 150-fold, from about 20-fold to about 50-fold, from about 30-fold to about 150-fold, from about 50-fold to about 100-fold, from about 70-fold to about-150 fold, from about 100-fold to about 150-fold, from about 10-fold to about 100-fold, from about 100-fold to about 200-fold, of the motor neuron number, neuromuscular junction (NMJ) electrophysiology (e.g., miniature end-plate potentials (mEPPs), end-plate potentials (EPPs), Quantal content), neurotransmission at the NMJ, muscle strength, etc. of the subject in the absence of the present composition and method.

The present composition and method may result in a decrease in the neurodegeneration, morphological abnormalities of the neuromuscular junctions (NMJs), etc. of the subject, where the neurodegeneration, morphological abnormalities of the neuromuscular junctions (NMJs), etc. of the subject affected by the present composition and method is no greater than 90%, no greater than 85%, no greater than 80%, no greater than 75%, no greater than 70%, no greater than 65%, no greater than 60%, no greater than 55%, no greater than 50%, no greater than 45%, no greater than 40%, no greater than 35%, no greater than 30%, no greater than 25%, no greater than 20%, no greater than 15%, no greater than 10%, about 10% to about 90%, about 15% to about 80%, about 20% to about 70%, about 25% to about 60%, about 30% to about 50%, about 30% to about 40%, about 25% to about 40%, about 20% to about 30%, about 25% to about 35%, about 10% to about 30%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 20% to about 50%, about 12.5% to about 80%, about 20% to about 70%, about 25% to about 60%, or about 25% to about 50%, about 1% to about 100%, about 5% to about 90%, about 10% to about 80%, about 5% to about 70%, about 5% to about 60%, about 10% to about 50%, about 15% to about 40%, about 5% to about 20%, about 1% to about 20%, about 10% to about 30%, about 5%, about 10%, about 20%, about 30%, about 40%, about 50%, about 60%, about 70%, about 80%, about 90%, about 100%, about 10% to about 90%, about 12.5% to about 80%, about 20% to about 70%, about 25% to about 60%, or about 25% to about 50%, of the neurodegeneration, morphological abnormalities of the neuromuscular junctions (NMJs), etc. of the subject in the absence of the present composition and method.

The present disclosure provides for a method of treating a neurodegenerative disorder, including motor neuron diseases, in a subject, the method comprising administering to the subject an agent that upregulates microautophagy (e.g., synaptic microautophagy).

The present method and composition may ameliorate the symptoms of a motor neuron disease in a subject. The present method and composition may result in at least partial correction of neuropathology and/or alleviation and/or prevention and/or stabilization and/or slowing of disease progression, and/or progression of the symptoms of the motor neuron disease. The present method and composition may prevent motor neuron death and muscle degeneration, and/or delay the onset of paralysis and death.

The present pharmaceutical composition may comprise, or consist essentially of (or consist of), a nucleic acid molecule encoding a mutant Hsp70 family member protein (e.g., Hspa8).

The present pharmaceutical composition may comprise, or consist essentially of (or consist of), a mutant Hsp70 family member protein (e.g., Hspa8).

The present pharmaceutical composition may comprise, or consist essentially of (or consist of), a modulator of an Hsp70 family member protein (e.g., Hspa8).

The present pharmaceutical composition may comprise, or consist essentially of (or consist of), a nucleic acid molecule encoding a modulator of an Hsp70 family member protein (e.g., Hspa8).

The present pharmaceutical composition (the nucleic acid molecule encoding the mutant Hsp70 family member protein (e.g., Hspa8), the mutant Hsp70 family member protein (e.g., Hspa8), the modulator of an Hsp70 family member protein (e.g., Hspa8), or a nucleic acid molecule encoding a modulator of an Hsp70 family member protein (e.g., Hspa8)) may be administered to the central nervous system (CNS) of the subject. The present pharmaceutical composition may be administered to the spinal cord or brain (e.g., the brainstem region) of the subject. The present pharmaceutical composition may be administered by intrathecal, intraventricular (known also as intracerebroventricular or ICV), intracranial, or intramuscular administration (e.g., injection). The present pharmaceutical composition may be administered to a particular ventricle, e.g., to the lateral ventricles or to the fourth ventricle of the brain. The present pharmaceutical composition may be administered by stereotaxic microinjection.

In one embodiment, the present pharmaceutical composition may be administered via a pump. Such pumps are commercially available, for example, from Alzet (Cupertino, Calif.) or Medtronic (Minneapolis, Minn.). The pump may be implantable. Another way to administer the present pharmaceutical composition is to use a cannula or a catheter.

The present pharmaceutical composition may be administered intrathecally, orally, intravenously, intramuscularly, topically, arterially, or subcutaneously.

The present composition and methods may be used to treat a neurodegenerative disorder, including motor neuron diseases. Non-limiting examples of motor neuron diseases include, spinal muscular atrophy (SMA), amyotrophic lateral sclerosis (ALS), spinal bulbar muscular atrophy (SBMA), hereditary spastic paraplegia (HSP), primary lateral sclerosis (PLS), progressive muscular atrophy (PMA), progressive bulbar palsy (PBP), and pseudobulbar palsy.

The present composition and methods may be used to treat a condition with defects in neurotransmission stemming from perturbed synaptic autophagy.

In certain embodiments, the present composition and methods may primarily act at the neuromuscular synapse, enhancing neurotransmission without a significant effect on SMN levels. In certain embodiments, the present composition and methods may increase SMN levels.

The present composition and methods may also be used to treat conditions including, but not limited to, spinal cerebellar ataxia, spinal muscular atrophy, traumatic spinal cord injury, and Tay-Sachs disease.

The present method may further comprise administering a SMN2 splicing modifier to the subject.

The heat shock protein may be an Hsp70 family member protein, including, but not limited to, Hspa8 (Hsp70-8, Hsc70), Hsp70, Hsp70-2, Hsp70-4, Hsp70-4L, Hsp70-5, Hsp70-6, Hsp70-7, Hsp70-9, Hsp70-12a, and Hsp70-14.

Heat shock 70 kDa protein 8 (Hspa8), also known as Hsp70-8 or Hsc70, is a heat shock protein that in humans is encoded by the HSPA8 gene on chromosome 11 (Gene ID 3312). The murine HSPA8 has a Gene ID of 15481. As a member of the heat shock protein 70 family and a chaperone protein, it facilitates the proper folding of newly translated and misfolded proteins, as well as stabilize or degrade mutant proteins. Its functions contribute to biological processes including signal transduction, apoptosis, autophagy, protein homeostasis, and cell growth and differentiation. Mayer et al., Hsp70 chaperones: cellular functions and molecular mechanism, Cellular and Molecular Life Sciences, 2005, 62 (6): 670-684. The Hsp70 proteins have three major functional domains: an N-terminal ATPase domain, a substrate binding domain, and a C-terminal domain.

The NCBI Reference Sequence (RefSeq) accession numbers for human Hspa8 mRNA may include NM_006597 and NM_153201. The NCBI RefSeq accession numbers for human Hspa8 protein may include NP_006588 and NP_694881. The NCBI RefSeq accession numbers for murine Hspa8 mRNA may include NM_031165 and NM_001364480. The NCBI RefSeq accession numbers for murine Hspa8 protein may include NP_112442 and NP_001351409.

There may be a number of different isoforms for each of these heat shock proteins discussed in this disclosure, provided herein are the general accession numbers, NCBI Reference Sequence (RefSeq) accession numbers, GenBank accession numbers, and/or UniProt numbers to provide relevant sequences. The proteins/polypeptides may also comprise other sequences. Any isoform and transcript variants of the Hsp70 family member protein (e.g., Hspa8) are encompassed by the present disclosure.

The present modulator may modulate the activity and/or level of any isoform of the heat shock protein (e.g., an Hsp70 family member protein such as Hspa8). The present modulator may modulate the activity and/or level of a wild-type or mutant heat shock protein (e.g., an Hsp70 family member protein such as Hspa8).

The term "Hspa8", "Hspa8" "HSPA8" or "HSPA8" is meant to include the DNA, RNA, mRNA, cDNA, recombinant DNA or RNA, or the protein arising from the gene. As used herein, Hspa8 can refer to the gene or the protein encoded by the gene, as appropriate in the specific context utilized. Additionally, in certain contexts, the reference will be to the mouse gene or protein, and in others the human gene or protein as appropriate in the specific context.

The present composition and methods may be used in combination with other therapeutic treatments for the condition, such as an agent that increases the level of SMN protein. For example, the agent may be a SMN2 splicing modifier. The SMN2 splicing modifier may act by shifting SMN2 pre-mRNA splicing toward the production of full length SMN mRNA. The SMN2 splicing modifier may modulate alternate splicing of the survival motor neuron 2 (SMN2) gene, functionally converting it into SMN1 gene, thus increasing the level of SMN protein in the CNS (e.g., Spinraza®). The other therapeutic treatments may inhibit glutamate release (e.g., riluzole). The other therapeutic treatments may be a metalloporphyrin that neutralizes reactive oxygen and nitrogen species. The other therapeutic treatments may be a JNK Inhibitor, or an antioxidant that scavenges reactive oxygen species (ROS) and inhibits proinflammatory responses.

The routes of administration of the pharmaceutical compositions include oral, intravenous, subcutaneous, intramuscular, inhalation, or intranasal administration. Additionally, specifically targeted delivery of the present composition (comprising, e.g., nucleic acid, peptide, or small molecule) could be delivered by targeted liposome, nanoparticle or other suitable means.

The amount and/or activity of an Hsp70 family member protein (e.g., Hspa8) may be downregulated by RNA interference or RNAi (such as small interfering RNAs or siRNAs, small hairpin RNAs or shRNAs, microRNAs or miRNAs, a double-stranded RNA (dsRNA), etc.), antisense molecules, and/or ribozymes targeting the DNA or mRNA encoding the an Hsp70 family member protein (e.g., Hspa8). The amount and/or activity of the an Hsp70 family member protein (e.g., Hspa8) may be downregulated by gene knockout. The amount and/or activity of an Hsp70 family member protein (e.g., Hspa8) may be downregulated by the cluster regularly interspaced short palindromic repeat-associated nuclease (CRISPR) technology.

The amount and/or activity of an Hsp70 family member protein (e.g., Hspa8) may be modulated by introducing polypeptides (e.g., antibodies) or small molecules which inhibit gene expression or functional activity of the an Hsp70 family member protein (e.g., Hspa8).

Agents that bind to or modulate, such as down-regulating the amount, activity or expression of an Hsp70 family member protein (e.g., Hspa8), may be administered to a subject or target cells. Such an agent may be administered in an amount effective to down-regulate expression and/or activity of the an Hsp70 family member protein (e.g., Hspa8), or by activating or down-regulating a second signal which controls the expression, activity or amount of the Hsp70 family member protein (e.g., Hspa8).

Methods and compositions of the present disclosure may be used for prophylaxis as well as treating a disease as described herein (such as a motor neuron disease).

For prophylaxis, the present composition may be administered to a subject in order to prevent the onset of one or more symptoms of a disease such as a motor neuron disease. In one embodiment, the subject is asymptomatic. A prophylactically effective amount of the agent or composition is administered to such a subject. A prophylactically effective amount is an amount which prevents the onset of one or more symptoms of the disease such as a motor neuron disease.

The present compositions may be used in vitro or administered to a subject. The administration may be topical, intravenous, intranasal, or any other suitable route as described herein.

The present methods may utilize adeno-associated virus (AAV) mediated gene delivery. Additionally, delivery vehicles such as nanoparticle- and lipid-based nucleic acid or protein delivery systems can be used as an alternative to viral vectors. Further examples of alternative delivery vehicles include lentiviral vectors, lipid-based delivery system, gene gun, hydrodynamic, electroporation or nucleofection microinjection, and biolistics. Various gene delivery methods are discussed in detail by Nayerossadat et al. (*Adv Biomed Res.* 2012; 1: 27) and Ibraheem et al. (*Int J Pharm.* 2014 Jan. 1; 459(1-2):70-83).

The present methods may use nanoparticle-based siRNA delivery systems. The nanoparticle-formulated siRNA delivery systems may be based on polymers or liposomes. Nanoparticles conjugated to the cell-specific targeting ligand for effective siRNA delivery can increase the chance of binding the cell surface receptor. The nanoparticles may be coated with PEG (polyethylene glycol) which can reduce uptake by the reticuloendothelial system (RES), resulting in enhanced circulatory half-life. Various nanoparticle-based delivery systems such as cationic lipids, polymers, dendrimers, and inorganic nanoparticles may be used in the present methods to provide effective and efficient siRNA delivery in vitro or in vivo.

The present composition may be administered by bolus injection or chronic infusion. The present composition may be administered directly into the central nervous system (CNS). The present composition may be administered systemically. The present composition may be administered by topical administration, intraocular administration, parenteral administration, intrathecal administration, subdural administration, and/or subcutaneous administration. The present composition may be administered at or near the site of the disease, disorder or injury, in an effective amount.

The present composition may be administered in a local or systemic manner, for example, via injection directly into the desired target site, e.g., in a depot or sustained release formulation. The composition may be administered in a targeted drug delivery system, for example, in liposomes or nanoparticles coated with tissue-specific or cell-specific ligands/antibodies. The liposomes or nanoparticles will be targeted to and taken up selectively by the desired tissue or cells. A summary of various delivery methods and techniques of siRNA administration in ongoing clinical trials is provided in Zuckerman and Davis 2015; Nature Rev. Drug Discovery, Vol. 14: 843-856, December 2015. In some embodiments, the level of an Hsp70 family member protein (e.g., Hspa8) is decreased in a desired target cell. The expression of the Hsp70 family member protein (e.g., Hspa8) may be specifically decreased only in the desired target cell (i.e., those cells which are predisposed to the condition, or exhibiting the disease already), and not substantially in other non-diseased cells. In these methods, expression of the Hsp70 family member protein (e.g., Hspa8) may not be substantially reduced in other cells, i.e., cells which are not desired target cells. Thus, in such embodiments, the level of the Hsp70 family member protein (e.g., Hspa8) remains substantially the same or similar in non-target cells in the course of or following treatment.

The vectors comprising the present nucleic acid may be delivered into host cells by a suitable method. Methods of delivering the present composition to cells may include transfection of nucleic acids or polynucleotides (e.g., using reagents such as liposomes or nanoparticles); electroporation, delivery of protein, e.g., by mechanical deformation (see, e.g., Sharei et al. *Proc. Natl. Acad. Sci. USA* (2013) 110(6): 2082-2087); or viral transduction. Exemplary viral vectors include, but are not limited to, recombinant retroviruses, alphavirus-based vectors, and adeno-associated virus (AAV) vectors. In some embodiments, the vectors are retroviruses. In some embodiments, the vectors are lentiviruses. In some embodiments, the vectors are adeno-associated viruses.

Vectors of the present disclosure can comprise any of a number of promoters known to the art, wherein the promoter is constitutive, regulatable or inducible, cell type specific, tissue-specific, or species specific. In addition to the sequence sufficient to direct transcription, a promoter sequence of the invention can also include sequences of other regulatory elements that are involved in modulating transcription (e.g., enhancers, kozak sequences and introns). Many promoter/regulatory sequences useful for driving constitutive expression of a gene are available in the art and include, but are not limited to, for example, CMV (cytomegalovirus promoter), EF1a (human elongation factor 1 alpha promoter), SV40 (simian vacuolating virus 40 promoter), PGK (mammalian phosphoglycerate kinase promoter), Ubc (human ubiquitin C promoter), human beta-actin promoter, rodent beta-actin promoter, CBh (chicken beta-actin promoter), CAG (hybrid promoter contains CMV enhancer, chicken beta actin promoter, and rabbit beta-globin splice acceptor), TRE (Tetracycline response element promoter), H1 (human polymerase III RNA promoter), U6 (human U6 small nuclear promoter), and the like. Moreover, inducible and tissue specific expression of an RNA, transmembrane proteins, or other proteins can be accomplished by placing the nucleic acid encoding such a molecule under the control of an inducible or tissue specific promoter/regulatory sequence. Examples of tissue specific or inducible promoter/regulatory sequences which are useful for this purpose include, but are not limited to, the rhodopsin promoter, the MMTV LTR inducible promoter, the SV40 late enhancer/promoter, synapsin 1 promoter, ET hepatocyte promoter, GS glutamine synthase promoter and many others. Various commercially available ubiquitous as well as tissue-specific promoters can be found at http://www.invivogen.com/prom-a-list and https://www.addgene.org/. In addition, promoters which are well known in the art can be induced in response to inducing agents such as metals, glucocorticoids, tetracycline, hormones, and the like, are also contemplated for use with the invention. Thus, it will be appreciated that the present disclosure includes the use of any promoter/regulatory sequence known in the art that is capable of driving expression of the desired protein operably linked thereto.

Vectors according to the present disclosure can be transformed, transfected or otherwise introduced into a wide variety of host cells. Numerous methods of transfection are known to the ordinarily skilled artisan, for example, lipofectamine, calcium phosphate co- precipitation, electroporation, DEAE-dextran treatment, microinjection, viral transduction, and other methods known in the art. Transduction refers to entry of a virus into the cell and expression (e.g., transcription and/or translation) of sequences delivered by the viral vector genome. In the case of a recombinant vector, "transduction" generally refers to entry of the recombinant viral vector into the cell and expression of a nucleic acid of interest delivered by the vector genome.

The administration regimen may depend on several factors, including the serum or tissue turnover rate of the therapeutic composition, the level of symptoms, and the accessibility of the target cells in the biological matrix. Preferably, the administration regimen delivers sufficient therapeutic composition to effect improvement in the target disease state, while simultaneously minimizing undesired side effects.

In accordance with the present disclosure, there may be numerous tools and techniques within the skill of the art, such as those commonly used in molecular immunology, cellular immunology, pharmacology, and microbiology (see, e.g., Sambrook et al. (2001) Molecular Cloning: A Laboratory Manual. 3rd ed. Cold Spring Harbor Laboratory Press: Cold Spring Harbor, N.Y.; Ausubel et al. eds. (2005) Current Protocols in Molecular Biology. John Wiley and Sons, Inc.: Hoboken, N.J.; Bonifacino et al. eds. (2005) Current Protocols in Cell Biology. John Wiley and Sons, Inc.: Hoboken, N.J.; Coligan et al. eds. (2005) Current Protocols in Immunology, John Wiley and Sons, Inc.: Hoboken, N.J.; Coico et al. eds. (2005) Current Protocols in Microbiology, John Wiley and Sons, Inc.: Hoboken, N.J.; Coligan et al. eds. (2005) Current Protocols in Protein Science, John Wiley and Sons, Inc.: Hoboken, N.J.; and Enna et al. eds. (2005) Current Protocols in Pharmacology, John Wiley and Sons, Inc.: Hoboken, N.J.)

As used herein, the term "modulator" refers to agents capable of modulating (e.g., down-regulating, decreasing, suppressing, or upregulating, increasing) the level/amount and/or activity of the heat shock protein (e.g., Hspa8).

As used herein, the term "inhibitor" refers to agents capable of down-regulating or otherwise decreasing or suppressing the level/amount and/or activity of the heat shock protein (e.g., Hspa8).

The mechanism of modulation may be at the genetic level (e.g., modulating such as interfering with, inhibiting, down-regulating, decreasing, suppressing, or upregulating, increasing, expression, transcription or translation, etc.) or at the protein level (e.g., binding, competition, etc.).

The mechanism of inhibition may be at the genetic level (e.g., interference with or inhibit expression, transcription or translation, etc.) or at the protein level (e.g., binding, competition, etc.).

The present modulators may be a small molecule, a polynucleotide, a polypeptide, or an antibody or antigen-binding portion thereof. In one embodiment, the polynucleotide is a small interfering RNA (siRNA) or an antisense molecule.

In one embodiment, the modulator is a CRISPR (clustered regularly interspaced short palindromic repeats)-Cas system specific for the heat shock protein (e.g., Hspa8).

A wide variety of suitable modulators may be employed, guided by art-recognized criteria such as efficacy, toxicity, stability, specificity, half-life, etc.

Modulators of Heat Shock Proteins

Small Molecule Modulators

As used herein, the term "small molecules" encompasses molecules other than proteins or nucleic acids without strict regard to size. Non-limiting examples of small molecules that may be used according to the methods and compositions of the present invention include, small organic molecules, peptide-like molecules, peptidomimetics, carbohydrates, lipids or other organic (carbon containing) or inorganic molecules.

Non-limiting examples of the present modulators of heat shock proteins include sulfogalactolipids (SGLs), sulfogalactosyl ceramide (SGC), and sulfogalactoglycerolipid (SGG). In one embodiment, the SGL, SGC, or SGG bind to the N-terminal ATPase-containing domain of an Hsp70 family member. Mamelak et al., Carbohydrate Research, 2001, 335(2):91-100.

Non-limiting examples of the present modulators of heat shock proteins include the compounds described in U.S. Pat. Nos. 10,052,325; 9,567,318; and U.S. Patent Publication No. 2009-0075948.

Non-limiting examples of the present modulators of autophagy (e.g., microautophagy such as synaptic microautophagy) include the compounds described in WO2017098467, and WO2014026372.

In certain embodiments, the inhibitor used in the present methods and compositions is a polynucleotide that reduces expression of an Hsp70 family member protein (e.g., Hspa8).

The nucleic acid target of the polynucleotides (e.g., siRNA, antisense oligonucleotides, and ribozymes) may be any location within the gene or transcript of an Hsp70 family member protein (e.g., Hspa8).

RNA Interference

SiRNAs (small interfering RNAs) or small-hairpin RNA (shRNA) may be used to modulate (e.g., decrease) the level of an Hsp70 family member protein (e.g., Hspa8).

SiRNAs may have 16-30 nucleotides, e.g., 16, 17, 18, 19, 20, 21, 22, 23, 24, 25, 26, 27, 28, 29, or 30 nucleotides. The siRNAs may have fewer than 16 or more than 30 nucleotides. The polynucleotides of the invention include both unmodified siRNAs and modified siRNAs such as siRNA derivatives etc.

SiRNAs can be delivered into cells in vitro or in vivo by methods known in the art, including cationic liposome transfection and electroporation. SiRNAs and shRNA molecules can be delivered to cells using viruses or DNA vectors.

Antisense Polynucleotides

In other embodiments, the polynucleotide is an antisense molecule that is complementary to a target region within the mRNA of an Hsp70 family member protein (e.g., Hspa8). The antisense polynucleotide may bind to the target region and inhibit translation. The antisense oligonucleotide may be DNA or RNA, or comprise synthetic analogs of ribodeoxynucleotides. Thus, the antisense oligonucleotide inhibits expression of an Hsp70 family member protein (e.g., Hspa8).

An antisense oligonucleotide can be, for example, about 7, 10, 15, 20, 25, 30, 35, 40, 45, 50, 55, 60, 65, 70, 75, 80, or more nucleotides in length.

The antisense nucleic acid molecules of the invention may be administered to a subject, or generated in situ such that they hybridize with or bind to the mRNA of an Hsp70 family member protein (e.g., Hspa8). Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using viruses or DNA vectors.

Ribozyme

In other embodiments, the polynucleotide is a ribozyme that inhibits expression of the gene of an Hsp70 family member protein (e.g., Hspa8).

Ribozymes can be chemically synthesized in the laboratory and structurally modified to increase their stability and catalytic activity using methods known in the art. Alternatively, ribozyme encoding nucleotide sequences can be introduced into host cells through gene-delivery mechanisms known in the art.

Other aspects of the invention include vectors (e.g., viral vectors, expression cassettes, plasmids) comprising or encoding polynucleotides of the subject invention (e.g., siRNA, antisense nucleic acids, and ribozymes), and host cells genetically modified with polynucleotides or vectors of the subject invention.

Polypeptides

The present modulators can be a polypeptide that modulates the activity and/or level of an Hsp70 family member protein (e.g., Hspa8). The modulator may be an inhibitor which is a polypeptide decreasing/inhibiting the activity and/or level of an Hsp70 family member protein (e.g., Hspa8).

Various means for delivering polypeptides to a cell can be utilized to carry out the methods of the subject invention. For example, protein transduction domains (PTDs) can be fused to the polypeptide, producing a fusion polypeptide, in which the PTDs are capable of transducing the polypeptide cargo across the plasma membrane (Wadia, J. S. and Dowdy, S. F., Curr. Opin. Biotechnol., 2002, 13(1)52-56).

According to the present methods, recombinant cells may be administered to a subject, wherein the recombinant cells have been genetically modified to express a nucleotide sequence encoding a modulatory or inhibitory polypeptide.

Antibodies

The present modulators can be an antibody or antigen-binding portion thereof that is specific to an Hsp70 family member protein (e.g., Hspa8).

The antibody or antigen-binding portion thereof may be the following: (a) a whole immunoglobulin molecule; (b) an scFv; (c) a Fab fragment; (d) an F(ab')2; and (e) a disulfide linked Fv. The antibody or antigen-binding portion thereof may be monoclonal, polyclonal, chimeric and humanized. The antibodies may be murine, rabbit or human antibodies.

Endonucleases

The Hsp70 family member protein (e.g., Hspa8) may be modulated (e.g., inhibited) by using a sequence-specific endonuclease that target the gene encoding the Hsp70 family member protein (e.g., Hspa8). Thus, the modulator (e.g., an inhibitor) of a Hsp70 family member protein (e.g., Hspa8) may comprise an endonuclease.

Non-limiting examples of the endonucleases include a zinc finger nuclease (ZFN), a ZFN dimer, a ZFNickase, a transcription activator-like effector nuclease (TALEN), or an RNA-guided DNA endonuclease (e.g., CRISPR/Cas9). Meganucleases are endonucleases characterized by their capacity to recognize and cut large DNA sequences (12 base pairs or greater). Any suitable meganuclease may be used in the present methods to create double-strand breaks in the host genome, including endonucleases in the LAGLIDADG and PI-Sce family An example of sequence-specific endonucleases includes RNA-guided DNA nucleases, e.g., the CRISPR/Cas system (Geurts et al., Science 325, 433 (2009); Mashimo et al., PLoS ONE 5, e8870 (2010); Carbery et al., Genetics 186, 451-459 (2010); Tesson et al., Nat. Biotech. 29, 695-696 (2011). Wiedenheft et al. Nature 482, 331-338 (2012); Jinek et al. Science 337, 816-821 (2012); Mali et al. Science 339, 823-826 (2013); Cong et al. Science 339, 819-823 (2013)).

Conditions to be Treated

The present compositions and methods modulate, correct, and/or augment motor function in a subject afflicted with a motor neuron disease or motor neuronal damage.

Conditions to be treated by the present compositions and methods include, but are not limited to, spinal muscular atrophy (SMA), amytrophic lateral sclerosis (ALS), spinal bulbar muscular atrophy (SBMA), spinal cerebellar ataxia, primary lateral sclerosis (PLS), or traumatic spinal cord injury, primary lateral sclerosis (PLS), progressive muscular atrophy (PMA), hereditary spastic paraparesis (HSP), X-linked spinobulbar muscular atrophy (SBMA; Kenney disease), progressive bulbar palsy, pseudo-bulbar palsy, post-polio syndrome (PPS), Huntington's disease, Essential tremor (ET), paralysis, and Parkinson's disease.

Without being limited as to theory, the pathology associated with motor neuron damage may include motor neuron degeneration, gliosis, neurofilament abnormalities, loss of myelinated fibers in corticospinal tracts and ventral roots. Two types of onset are recognized: bulbar onset, which affects brainstem motor neurons, (affects the facial muscles, speech, and swallowing); and limb onset, which affects spinal cord motor neurons, is reflected by spasticity, generalized weakness, muscular atrophy, paralysis, and respiratory failure. In ALS, subjects have both bulbar and limb onset. In PLS, subjects have bulbar onset.

In some embodiments, the present composition may decrease or prevent a particular symptom associated with decreased motor neuron function. For example, the present composition and method may improve, stabilize, or prevent muscle atrophy, muscle weakness, fasciculation, fibrillation, hypotonia, hyporeflexia, weakness, hypertonia, hyperreflexia, clonus, paralysis (e.g., quadriplegia, paraplegia, or monoplegia), spasticity, Babinski test, resting, tremors, athetosis, chorea, ballismus, tardive dyskinesia, rigidity, dystonia, ataxia, dysmetria, dysdiadochokinesia, nystagmus, delay in initiating movements, bradykinesia, or other movement disorders.

Recombinant AAV Vectors

In certain embodiments, the nucleic acid is provided in a recombinant adeno- associated virus (AAV) vector. In additional embodiments, the AAV vector further comprises a chicken Beta-actin promoter and wherein the AAV is capable of crossing the blood-brain barrier (BBB). In yet additional embodiments, the AAV is AAV8 or AAV9.

For example, an AAV vector may be administered at or near the axon terminals of neurons. The neurons internalize the AAV vector and transport it in a retrograde manner along the axon to the cell body. Similar properties of adenovirus, HSV, and pseudo-rabies virus have been shown to deliver genes to distal structures within the brain (Soudas et al. (2001) FASEB J. 15:2283-2285; Breakefield et al. (1991) New Biol. 3:203-218; and deFalco et al. (2001) Science, 291:2608-2613).

In aspects where gene transfer is mediated by a DNA viral vector, such as an adenovirus (Ad) or adeno-associated virus (AAV), a vector construct refers to the polynucleotide comprising the viral genome or part thereof, and a transgene. Suitable neurotrophic viral vectors for the practice of this invention include, but are not limited to adeno-associated viral vectors (AAV), herpes simplex viral vectors and lentiviral vectors.

AAV of any serotype can be used. The serotype of the viral vector used in certain embodiments of the invention may be AAV1, AAV2, AAV3, AAV4, AAV5, AAV6, AAV7, AAV8, and AAV9 (see, e.g., Gao et al. (2002) PNAS, 99:11854-11859; and Viral Vectors for Gene Therapy: Methods and Protocols, ed. Machida, Humana Press, 2003). Other serotype besides those listed herein can be used. Furthermore, pseudotyped AAV vectors may also be utilized in the methods described herein. Pseudotyped AAV vectors are those which contain the genome of one AAV serotype in the capsid of a second AAV serotype; for example, an AAV vector that contains the AAV2 capsid and the AAV1 genome or an AAV vector that contains the AAV5 capsid and the AAV2 genome (Auricchio et al., (2001) Hum. Mol. Genet., 10(26):3075-81).

In certain embodiments, the concentration or titer of the vector in the composition is at least: (a) 5, 6, 7, 8, 9, 10, 15, 20, 25, or $50(\times 10^{12}$ gp/ml); (b) 5, 6, 7, 8, 9, 10, 15, 20, 25, or $50(\times 10^{9}$ to/ml); or (c) 5, 6, 7, 8, 9, 10, 15, 20, 25, or $50(\times 10^{10}$ iu/ml).

In experimental mice, the total volume of injected AAV solution is for example, between 1 to 20 µl. For other mammals, including the human brain, volumes and delivery rates are appropriately scaled. For example, it has been demonstrated that volumes of 150 µl can be safely injected in the primate brain (Janson et al. (2002) Hunt. Gene Ther. 13:1391-1412). Treatment may consist of a single injection per target site, or may be repeated in one or more ventricles. Suitable ventricles include the lateral ventricles, third ventricle, and the fourth ventricle. Multiple injection sites can be used. For example, in some embodiments, in addition to the first administration site, a composition containing a viral vector carrying a transgene is administered to another site which can be contralateral or ipsilateral to the first administration site. Injections can be single or multiple, unilateral or bilateral.

In addition to the elements identified above for recombinant AAV vectors, the vector may also include conventional control elements which are operably linked to the transgene in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

As used herein, a nucleic acid sequence and regulatory sequences are said to be operably linked when they are covalently linked in such a way as to place the expression or transcription of the nucleic acid sequence under the influence or control of the regulatory sequences. If it is desired that the nucleic acid sequences be translated into a functional protein, two DNA sequences are said to be operably linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably linked to a nucleic acid sequence if the promoter region were capable of effecting transcription of that DNA sequence such that the resulting transcript might be translated into the desired protein or polypeptide. Similarly two or more coding regions are operably linked when they are linked in such a way that their transcription from a common promoter results in the expression of two or more proteins having been translated in frame. In some embodiments, operably linked coding sequences yield a fusion protein. In some embodiments, operably linked coding sequences yield a functional RNA (e.g., shRNA, miRNA).

For nucleic acids encoding proteins, a polyadenylation sequence generally is inserted following the transgene sequences and before the 3' AAV ITR sequence. An AAV construct useful in the present invention may also contain an intron, desirably located between the promoter/enhancer sequence and the transgene. One possible intron sequence is derived from SV-40, and is referred to as the SV-40 T intron sequence. Another vector element that may be used is an internal ribosome entry site (IRES). An IRES sequence is used to produce more than one polypeptide from a single gene transcript. An IRES sequence would be used to produce a protein that contain more than one polypeptide chains. Selection of these and other common vector elements are conventional and many such sequences are available (see, e.g., Sambrook et al, and references cited therein at, for example, pages 3.18 3.26 and 16.17 16.27 and Ausubel et al., Current Protocols in Molecular Biology, John Wiley & Sons, New York, 1989). In some circumstances, a Foot and Mouth Disease Virus 2A sequence may be included in a polyprotein; this is a small peptide (approximately 18 amino acids in length) that has been shown to mediate the cleavage of polyproteins. The cleavage activity of the 2A sequence has previously been demonstrated in artificial systems including plasmids and gene therapy vectors (AAV and retroviruses) (Ryan et al., EMBO, 1994; 4: 928-933; Mattion et al., J Virology, November 1996; p. 8124-8127; Furler et al., Gene Therapy, 2001; 8: 864-873; and Halpin et al., The Plant Journal, 1999; 4: 453-459; de Felipe et al., Gene Therapy, 1999; 6: 198-208; de Felipe et al., Human Gene Therapy, 2000; 11: 1921-1931.; and Klump et al., Gene Therapy, 2001; 8: 811-817).

The precise nature of the regulatory sequences needed for gene expression in host cells may vary between species, tissues or cell types, but shall in general include, as necessary, 5' non-transcribed and 5' non-translated sequences involved with the initiation of transcription and translation respectively, such as a TATA box, capping sequence, CAAT sequence, enhancer elements, and the like. Especially, such 5' non-transcribed regulatory sequences will include a promoter region that includes a promoter sequence for transcriptional control of the operably joined gene. Regulatory sequences may also include enhancer sequences or upstream activator sequences as desired. The vectors may optionally include 5' leader or signal sequences.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) (see, e.g., Boshart et al, Cell, 41:521-530 (1985)), the SV40 promoter, the dihydrofolate reductase promoter, the 13-actin promoter, the phosphoglycerol kinase (PGK) promoter, and the EF1a promoter [Invitrogen].

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al., Proc. Natl. Acad. Sci. USA, 93:3346-3351 (1996)), the tetracycline-repressible system (Gossen et al. (1992) Proc. Natl. Acad. Sci. USA, 89:5547-5551), the tetracycline-inducible system (Gossen et al. (1995) Science, 268:1766-1769, see also Harvey et al. (1998) Curr. Opin. Chem. Biol., 2:512-518), the RU486-inducible system (Wang et al. (1997) Nat. Biotech., 15:239-243 and Wang et al. (1997) Gene Ther., 4:432-441) and the rapamycin-inducible system (Magari et al. (1997) J. Clin. Invest., 100:2865-2872). Still other types of inducible promoters which may be useful in this context are those which are regulated by a specific physiological state, e.g., temperature, acute phase, a particular differentiation state of the cell, or in replicating cells only.

In another embodiment, the native promoter, or fragment thereof, for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner Such tissue-specific regulatory sequences (e.g., promoters, enhancers) are well known in the art. Exemplary tissue-specific regulatory sequences include but are not limited to the following tissue specific promoters: neuronal such as neuron-specific enolase (NSE) promoter (Andersen et al. (1993) Cell. Mol. Neurobiol., 13:503-15), neurofilament light-chain gene promoter (Piccioli et al. (1991) Proc. Natl. Acad. Sci. USA, 88:5611-5), and the neuron-specific vgf gene promoter (Piccioli et al. (1995) Neuron, 15:373-84). In some embodiments, the tissue-specific promoter is a promoter of a gene selected from:

neuronal nuclei (NeuN), glial fibrillary acidic protein (GFAP), adenomatous polyposis coli (APC), and ionized calcium-binding adapter molecule 1 (Iba-1). In some embodiments, the promoter is a chicken Beta-actin promoter.

Methods for obtaining recombinant AAVs having a desired capsid protein have been described (See, for example, US 2003/0138772, the contents of which are incorporated herein by reference in their entirety). A number of different AAV capsid proteins have been described, for example, those disclosed in Gao et al. (2004) *J. Virol*, 78(12):6381-6388; Gao et al. (2004) *Proc Natl Acad Sci USA*, 100(10):6081-6086. For the desired packaging of the presently described constructs and methods, the AAV9 vector and capsid is preferred. However, it is noted that other suitable AAVs such as rAAVrh.8 and rAAVrh.10, or other similar vectors may be adapted for use in the present invention. Typically the methods involve culturing a host cell which contains a nucleic acid sequence encoding an AAV capsid protein or fragment thereof; a functional rep gene; a recombinant AAV vector composed of AAV inverted terminal repeats (ITRs) and a transgene; and sufficient helper functions to permit packaging of the recombinant AAV vector into the AAV capsid proteins.

The components to be cultured in the host cell to package a rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters.

The recombinant AAV vector, rep sequences, cap sequences, and helper functions for producing the AAV may be delivered to the packaging host cell using any appropriate genetic element (vector). The selected genetic element may be delivered by any suitable method, including those described herein. See, e.g., Fisher et al. (1993) *J. Virol.*, 70:520-532 and U.S. Pat. No. 5,478,745.

In some embodiments, recombinant AAVs may be produced using the triple transfection method (e.g., as described in detail in U.S. Pat. No. 6,001,650). Typically, the recombinant AAVs are produced by transfecting a host cell with a recombinant AAV vector (comprising a transgene) to be packaged into AAV particles, an AAV helper function vector, and an accessory function vector. An AAV helper function vector encodes the "AAV helper function" sequences (i.e., rep and cap), which function in trans for productive AAV replication and encapsidation. Preferably, the AAV helper function vector supports efficient AAV vector production without generating any detectable wild-type AAV virions (i.e., AAV virions containing functional rep and cap genes). Non-limiting examples of vectors suitable for use with the present invention include pHLP19, described in U.S. Pat. No. 6,001,650 and pRep6cap6 vector, described in U.S. Pat. No. 6,156,303. The accessory function vector encodes nucleotide sequences for non-AAV derived viral and/or cellular functions upon which AAV is dependent for replication (i.e., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus.

Pharmaceutical Compositions and Administration

The pharmaceutical compositions can further comprise one or more pharmaceutically acceptable excipient, ligand, a conjugate, a vector, a lipid, a nanoparticle, a liposome, a carrier, an adjuvant or a diluent.

Delivery vehicles such as liposomes, nanocapsules, microparticles, microspheres, lipid particles, vesicles, and the like can be used to deliver the nucleic acid molecules described herein.

The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868; and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

Alternatively, nanocapsule or nanoparticle formulations may be used. Nanocapsules can generally entrap substances in a stable and reproducible way. Nanoparticles can be used to transport drugs through the BBB when administered intravenously as well as the factors that influence its transportation.

NPs are colloidal carriers that can have a natural or synthetic origin and can vary from 1 to 1000 nm in size. Synthetic NPs may be prepared from polymeric materials such as poly(ethylenimine) (PEI), poly(alkylcyanoacrylates), poly(amidoamine) dendrimers (PAMAM), poly(ε-caprolactone) (PCL), poly(lactic-co-glycolic acid) (PLGA), polyesters (poly(lactic acid) (PLA), or from inorganic materials such as gold, silicon dioxide (silica), among others. These carriers can transport drugs by adsorbing, entrapping or bounding covalently to them. Natural NPs are produced from natural polymers, such as polysaccharides (chitosan and alginate), amino acids (poly(lysine), poly(aspartic acid) (PASA)), or proteins (gelatin and albumin). Natural NPs have the advantage of providing biological signals to interact with specific receptors/transporters expressed by endothelial cells.

A number of ligands have been conjugated to NPs to facilitate BBB penetration. Such molecules can be grouped into four different types: (i) ligands that mediate the adsorption of proteins from the bloodstream that interact directly with BBB receptors or transporters; (ii) ligands that have direct interaction per se with BBB receptors or transporters; (iii) ligands that increase charge and hydrophobicity; and (iv) ligands that improve blood circulation time (e.g. PEG).

Other methods for assisting the NPs to cross the blood-brain barrier would include but are not limited to receptor mediated transport, transporter mediated transport, absorptive mediated transport, and cell penetrating transport.

Mammalian virus vectors that can be used to deliver RNA include oncoretroviral vectors, adenovirus vectors, Herpes simplex virus vectors, and lentiviruses.

In particular, HSV vectors are tropic for the central nervous system (CNS) and can establish lifelong latent infections in neurons.

The AAVs may be delivered to a subject in compositions according to any appropriate methods known in the art. The AAV, preferably suspended in a physiologically compatible carrier (e.g., in a composition), may be administered to a subject, e.g., a human, mouse, rat, cat, dog, sheep, rabbit, horse, cow, goat, pig, guinea pig, hamster, chicken, turkey, or a non-human primate. In certain embodiments, compositions may comprise an AAV alone, or in combination with one or more other viruses (e.g., a second AAV encoding having one or more different transgenes).

Suitable carriers may be readily selected by one of skill in the art in view of the indication for which the AAV is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present invention.

Optionally, the compositions of the invention may contain, in addition to the AAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The dose of AAV virions required to achieve a desired effect or "therapeutic effect," e.g., the units of dose in vector genomes/per kilogram of body weight (vg/kg), will vary based on several factors including, but not limited to: the route of AAV administration, the level of gene or RNA expression required to achieve a therapeutic effect, the specific disease or disorder being treated, and the stability of the gene or RNA product. One of skill in the art can readily determine an AAV virion dose range to treat a subject having a particular disease or disorder based on the aforementioned factors, as well as other factors that are well known in the art. An effective amount of the AAV is generally in the range of from about 10 µl to about 100 ml of solution containing from about $10^9$ to $10^{16}$ genome copies per subject. Other volumes of solution may be used. The volume used will typically depend, among other things, on the size of the subject, the dose of the AAV, and the route of administration. For example, for intrathecal or intracerebral administration a volume in range of 1 µl to 10 µl or 10 µl to 100 µl may be used. For intravenous administration a volume in range of 10 µl to 100 µl, 100 µl to 1 ml, 1 ml to 10 ml, or more may be used. In some cases, a dosage between about $10^{10}$ to $10^{12}$ AAV genome copies per subject is appropriate. In certain embodiments, $10^{12}$ AAV genome copies per subject is effective to target CNS tissues. In some embodiments the AAV is administered at a dose of $10^{10}$, $10^{11}$, $10^{12}$, $10^{13}$, $10^{14}$, or $10^{15}$ genome copies per subject. In some embodiments the AAV is administered at a dose of $10^{10}$, $10^{11}$, $10^{12}$, $10^{13}$, or $10^{14}$ genome copies per kg.

In some embodiments, AAV compositions are formulated to reduce aggregation of AAV particles in the composition, particularly where high AAV concentrations are present (e.g., about $10^{13}$ GC/ml or more). Methods for reducing aggregation of AAVs are well known in the art and, include, for example, addition of surfactants, pH adjustment, salt concentration adjustment, etc. (See, e.g., Wright et al. (2005) *Molecular Therapy* 12:171-178.)

Formulation of pharmaceutically-acceptable excipients and carrier solutions is well-known to those of skill in the art, as is the development of suitable dosing and treatment regimens for using the particular compositions described herein in a variety of treatment regimens. Typically, these formulations may contain at least about 0.1% of the active ingredient or more, although the percentage of the active ingredient(s) may, of course, be varied and may conveniently be between about 1 or 2% and about 70% or 80% or more of the weight or volume of the total formulation. Naturally, the amount of active ingredient in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition). Some variation in dosage will necessarily occur depending on the condition of the host. The person responsible for administration will, in any event, determine the appropriate dose for the individual host.

Sterile injectable solutions are prepared by incorporating the active AAV in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The AAV compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the AAV compositions of the present invention into suitable host cells. In particular, the AAV vector delivered components may be formulated for delivery either encapsulated in a lipid particle, a liposome, a vesicle, a nanosphere, or a nanoparticle or the like.

In addition to the methods of delivery described above, the following techniques are also contemplated as alternative methods of delivering the AAV compositions to a host. Sonophoresis (i.e., ultrasound) has been used and described in U.S. Pat. No. 5,656,016 as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations, transdermal matrices (U.S. Pat. Nos. 5,770,219 and 5,783,208) and feedback-controlled delivery (U.S. Pat. No. 5,697,899).

To prepare the present pharmaceutical compositions, a conjugate, a vector, a lipid, a nanoparticle, a liposome, an adjuvant or a diluent may be further admixed with a pharmaceutically acceptable carrier or excipient. See, e.g., *Remington's Pharmaceutical Sciences* and *U.S. Pharmacopeia: National Formulary*, Mack Publishing Company, Easton, Pa. (1984).

Formulations of therapeutic agents may be prepared by mixing with acceptable carriers, excipients, or stabilizers in the form of, e.g., lyophilized powders, slurries, aqueous solutions or suspensions (see, e.g., Hardman, et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.).

Toxicity and therapeutic efficacy of the therapeutic compositions, administered alone or in combination with another agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index ($LD_{50}/ED_{50}$). In particular aspects, therapeutic compositions exhibiting high therapeutic indices are desirable. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration.

The mode of administration can vary. Suitable routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial.

In particular embodiments, the composition or therapeutic can be administered by an invasive route such as by injection. In further embodiments of the invention, the composition, therapeutic, or pharmaceutical composition thereof, is administered intravenously, subcutaneously, intramuscularly, intraarterially, intra-articularly (e.g. in arthritis joints), intratumorally, or by inhalation, aerosol delivery. Administration by non-invasive routes (e.g., orally; for example, in a pill, capsule or tablet) is also within the scope of the present invention.

In order to overcome any issue of the pharmacological agents crossing the blood/brain barrier, intrathecal administration is a further preferred form of administration. Intrathecal administration involves injection of the drug into the spinal canal, more specifically the subarachnoid space such that it reaches the cerebrospinal fluid. This method is commonly used for spinal anesthesia, chemotherapy, and pain medication. Intrathecal administration can be performed by lumbar puncture (bolus injection) or by a port-catheter system (bolus or infusion). The catheter is most commonly inserted between the laminae of the lumbar vertebrae and the tip is threaded up the thecal space to the desired level (generally L3-L4). Intrathecal formulations most commonly use water, and saline as excipients but EDTA and lipids have been used as well.

Compositions can be administered with medical devices known in the art. For example, a pharmaceutical composition of the invention can be administered by injection with a hypodermic needle, including, e.g., a prefilled syringe or autoinjector.

The pharmaceutical compositions of the invention may also be administered with a needleless hypodermic injection device; such as the devices disclosed in U.S. Pat. Nos. 6,620,135; 6,096,002; 5,399,163; 5,383,851; 5,312,335; 5,064,413; 4,941,880; 4,790,824 or 4,596,556.

Alternately, one may administer the pharmaceutical composition in a local rather than systemic manner, for example, via injection of directly into the desired target site, often in a depot or sustained release formulation. Furthermore, one may administer the composition in a targeted drug delivery system, for example, in a liposome coated with a tissue-specific antibody, targeting, for example, the brain. The liposomes will be targeted to and taken up selectively by the desired tissue.

The administration regimen depends on several factors, including the serum or tissue turnover rate of the therapeutic composition, the level of symptoms, and the accessibility of the target cells in the biological matrix. Preferably, the administration regimen delivers sufficient therapeutic composition to effect improvement in the target disease state, while simultaneously minimizing undesired side effects. Accordingly, the amount of biologic delivered depends in part on the particular therapeutic composition and the severity of the condition being treated.

Determination of the appropriate dose is made by the clinician, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. In general, it is desirable that a biologic that will be used is derived from the same species as the animal targeted for treatment, thereby minimizing any immune response to the reagent.

As used herein, the terms "therapeutically effective amount", "therapeutically effective dose" and "effective amount" refer to an amount of the present nucleic acid molecules, mutant proteins/polypeptides, and/or modulators that, when administered alone or in combination with an additional therapeutic agent to a cell, tissue, or subject, is effective to cause a measurable improvement in one or more symptoms of a disease or condition or the progression of such disease or condition. A therapeutically effective dose further refers to that amount of the agent sufficient to result in at least partial amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. An effective amount of a therapeutic will result in an improvement of a diagnostic measure or parameter by at least 10%; usually by at least 20%; preferably at least about 30%; more preferably at least 40%, and most preferably by at least 50%. An effective amount can also result in an improvement in a subjective measure in cases where subjective measures are used to assess disease severity. The present agents/compositions may prevent or delay onset or amelioration of symptoms of the condition in a subject or an attainment of a desired biological outcome, such as correction of neuropathology, e.g., cellular pathology associated with a motor neuronal disease.

Kits

The present invention also provides kits comprising the present composition/agent (nucleic acid molecules, mutant proteins/polypeptides, and/or modulators) in kit form. A kit of the present invention includes one or more components described herein, in association with one or more additional components including, but not limited to a pharmaceutically acceptable ligand, a conjugate, a vector, a lipid, a nanoparticle, a liposome, an adjuvant, a diluent, carrier or excipient.

If the kit includes a pharmaceutical composition for parenteral administration to a subject, the kit can include a device for performing such administration. For example, the kit can include one or more hypodermic needles or other injection devices as discussed above.

The kit can include a package insert including information concerning the pharmaceutical compositions and dosage forms in the kit. Generally, such information aids patients and physicians in using the enclosed pharmaceutical compositions and dosage forms effectively and safely. For example, the following information regarding a combination of the invention may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references, manufacturer/distributor information and patent information.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

"Activation," "stimulation," and "treatment," as it applies to cells or to receptors, may have the same meaning, e.g., activation, stimulation, or treatment of a cell or receptor with a ligand, unless indicated otherwise by the context or explicitly. "Ligand" encompasses natural and synthetic ligands, e.g., cytokines, cytokine variants, analogues, muteins, and binding compounds derived from antibodies. "Ligand" also encompasses small molecules, e.g., peptide mimetics of cytokines and peptide mimetics of antibodies. "Activation" can refer to cell activation as regulated by internal mechanisms as well as by external or environmental factors. "Response," e.g., of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. "Administration" and "treatment" can refer, e.g., to therapeutic, pharmacokinetic, diagnostic, research, and experimental methods. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell. The term "subject" includes any organism, preferably an animal, more preferably a mammal (e.g., rat, mouse, dog, cat, rabbit) and most preferably a human, including a human patient.

"Treat" or "treating" means to administer a therapeutic agent, such as a composition containing any of the nucleic acid or AAV constructs or compositions of the present invention, internally or externally to a subject or patient having one or more disease symptoms, or being suspected of having a disease or being at elevated at risk of acquiring a disease, for which the agent has therapeutic activity. Typically, the agent is administered in an amount effective to alleviate one or more disease symptoms in the treated subject or population, whether by inducing the regression of or inhibiting the progression of such symptom(s) by any clinically measurable degree. The amount of a therapeutic agent that is effective to alleviate any particular disease symptom (also referred to as the "therapeutically effective amount") may vary according to factors such as the disease state, age, and weight of the patient, and the ability of the drug to elicit a desired response in the subject Whether a disease symptom has been alleviated can be assessed by any clinical measurement typically used by physicians or other skilled healthcare providers to assess the severity or progression status of that symptom.

The phrase "therapeutically effective amount" is used herein to mean an amount sufficient to cause an improvement in a clinically significant condition in the subject, or delays or minimizes or mitigates one or more symptoms associated with the disease, or results in a desired beneficial change of physiology in the subject.

"Isolated nucleic acid molecule" means a DNA or RNA of genomic, mRNA, cDNA, or synthetic origin or some combination thereof which is not associated with all or a portion of a polynucleotide in which the isolated polynucleotide is found in nature or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty or more other proteins or portions or fragments thereof or may include operably linked regulatory sequences that control expression of the coding region of the recited nucleic acid sequences, and/or may include vector sequences.

The term "vector" includes any genetic element, such as a plasmid, phage, transposon, cosmid, chromosome, artificial chromosome, virus, or virion, which is capable of replication when associated with the proper control elements and which can transfer gene sequences between cells. Thus, the term includes cloning and expression vehicles, as well as viral vectors. In some embodiments, useful vectors are contemplated to be those vectors in which the nucleic acid segment to be transcribed is positioned under the transcriptional control of a promoter.

The phrase "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers.

A "promoter" refers to a DNA sequence recognized by the synthetic machinery of the cell, or introduced synthetic machinery, required to initiate the specific transcription of a gene.

The phrases "operatively positioned," "operatively linked," "under control," or "under transcriptional control" means that the promoter is in the correct location and orientation in relation to the nucleic acid to control RNA polymerase initiation and expression of the gene.

The term "expression vector or construct" means any type of genetic construct containing a nucleic acid in which part or all of the nucleic acid encoding sequence is capable of being transcribed. In some embodiments, expression includes transcription of the nucleic acid, for example, to generate a biologically-active polypeptide product or inhibitory RNA (e. g., shRNA, miRNA) from a transcribed gene.

The present invention may be better understood by reference to the following non-limiting examples, which are presented in order to more fully illustrate the preferred embodiments of the invention. They should in no way be construed to limit the broad scope of the invention.

EXAMPLE 1

Spinal muscular atrophy (SMA) is a common, frequently fatal, neuromuscular disorder caused by mutations in the Survival of Motor Neuron 1 (SMN1) gene and, consequently, a paucity of the SMN protein. In humans, an almost identical copy gene, SMN2, is unable to fully compensate for loss of SMN1 owing to a splicing defect and thus an inability to express sufficient protein to stave off disease. How low SMN protein evolves into the SMA phenotype, selectively triggering motor neuron death and preferentially disabling the neuromuscular system is to be elucidated. Identifying mediators that provide a logical explanation for why splicing defects cause SMA or, uncovering additional, more disease-relevant SMN functions is therefore important.

We exploit a novel line of SMA mice in which early mortality, motor neuron loss and a severe phenotype are replaced by prolonged survival, intact motor neurons and a decidedly mild phenotype. Our results show that a spontaneous mutation in a chaperone protein that the mice express suppresses the SMA phenotype. We extend this finding to determine how the chaperone modulates the effects of low SMN.

We discovered that the heat shock chaperone protein, Hspa8, has a marked mitigating effect on the severe SMA phenotype. In model mice affected with the disease, a single amino acid change in Hspa8, is highly protective, preventing motor neuron death, precluding muscle denervation and arresting the inexorable onset of paralysis and death that characterizes spinal muscular atrophy. Accordingly, altering Hspa8 function can serve as disease-modifying treatment for SMA and other motor neurons diseases as well.

Validating the chaperone that we have identified as the bona fide mediator (suppressor) of the SMA phenotype could assign a novel role to the SMN protein—in synaptic micro-autophagy.

Despite recent progress in the quest to treat SMA, very little is known about what mediates the selective detrimental effects of low SMN on spinal motor neurons (MNs). Genetic screens constitute one useful strategy to identify relevant mediators. We have used such a screen to identify a ~4 Mbp region of mouse chromosome 9 that harbors a potent suppressor of the SMA phenotype. Our studies show that a chaperone-expressing gene in this region, invariably mutated in mice with the modified disease phenotype, is the critical suppressor. We will introduce the mutant chaperone into SMA mice and examine the resulting phenotype of the mutants using an array of molecular, cellular and behavioral analyses.

Marked Suppression of the Severe Disease Phenotype in SMA Model Mice

Mice devoid of the murine Smn gene but engineered to harbor 2 copies of the human SMN2 gene express little SMN protein and, as a consequence, suffer motor neuron loss and muscle paralysis during early postnatal life, succumbing to respiratory distress within the first two weeks of life. Restoring SMN to SMA mice shortly after birth enhances the protein in motor neurons and prevents their degeneration, improves motor performance and greatly increases lifespan (FIGS. 1A-1D).

Notwithstanding the generally severe disease phenotype and reduced lifespan of SMA mice, we found that some mutants died within a couple of days of birth while others survived into the third postnatal week of life. In an attempt to overcome these variations, we generated congenic SMA mice on each of the C57Bl/6 and FVB/N genetic strain backgrounds. Interestingly, the latter strain somewhat mitigated the severity of the disease [Mean lifespan on FVB/N strain=6.7±0.8 days; C57Bl/6 strain=0.63±0.13 days] while F1 mutants [Mean survival=11.04±1.4 days] were less severely affected than SMA mice on either parental strain background. These observations suggested the presence of strain-specific disease modifying genes.

The Chaperone, Hspa8, as a Major Determinant (Suppressor) of the Mild SMA Phenotype Considering the frequency (~6% of all mutants; ~1.5% of all F2 progeny) with which we obtained the mild SMA mutants, we assumed that there are likely two critical, recessive mediators that must be inherited simultaneously to mitigate the disease phenotype in our SMND7 SMA model mice. To map and identify the mediators (suppressors), we conducted a genome-wide association analysis using a panel of 150 single nucleotide polymorphic (SNP) markers informative for the parental (FVB/N and C57Bl/6) strains. We found significant linkage (LOD score >3.0) between the mild phenotype and mouse chromosome 9. We then conducted a more detailed analysis by repeating the genotyping using a panel of 1500 SNP markers. This confirmed our earlier results, narrowing down our region of interest (ROI) to a ~19 Mbp stretch between 48 Mbp and 29 Mbp. All of the mild mutants analyzed were homozygous C57Bl/6 for this region of chromosome 9. In contrast, only 2 of 13 typically affected mutants (as assessed by survival phenotypes) were homozygous for this region. To further delimit the ROI and to determine if it is sufficient to suppress severe SMA, we first backcrossed mice harboring this region to SMA carrier mice on the pure FVB/N strain over 6 successive generations, selecting for the 19 Mbp region from C57Bl/6 at each generation. At generation 6, SMA carriers that also carried the 19 Mbp ROI were assessed for strain purity and animals that were pure FVB/N save for the C57Bl/6 ROI, which was in a heterozygous state, bred to generate SMA mutants. As expected, 25% of the SMA mutants from these carriers exhibited the mild phenotype suggesting that the ROI does indeed harbor a suppressor. Recombinants among these mutants were then used to further refine the ROI. Four such mutants have allowed us to identify a ~4 Mbp region of chromosome 9 between 44 Mbp and 40 Mbp that is necessary to confer a mild phenotype on the SMA mutants.

Whole genome sequence analysis of the ~4 Mbp region in each of 5 mild SMA mutants and 5 severely affected littermates revealed 14 non-synonymous changes, in a total of 12 genes, which were consistently different between the two cohorts. Of the missense mutations in the remaining 11 genes, we turned our attention to a G470R change in the chaperone, Hspa8. We discovered that this change was not present in either the severe SMA mutants or the reference (C57Bl/6) sequence, suggesting that it is a mutation that arose spontaneously in our C57Bl/6 colony. Using gene-specific primers, we confirmed the presence of the mutation in all of our mild mutants and then discovered that the native amino acid (glycine) at this position is not just conserved in 15 commonly used strains of inbred mice, but is also conserved across species from humans to worms. This suggests an important function for the domain harboring the mutation.

Figure 2:
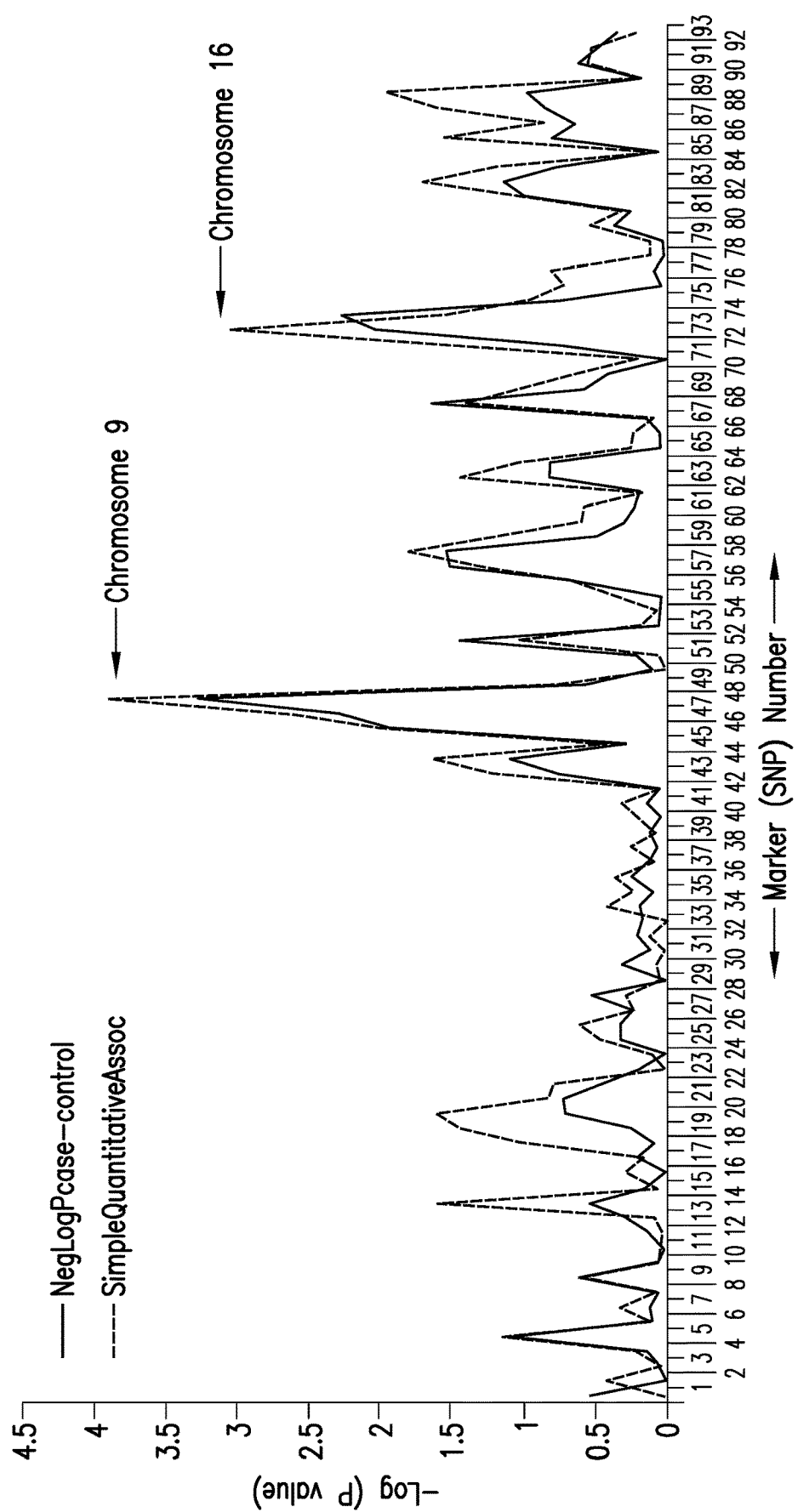
FIG. 2. Linkage analysis scores. A genome-wide SNP analysis of a limited cohort of F2 "typical" and "modified" mutants by two independent methods indicates linkage of the modified phenotype to loci on chromosomes 9 and 16.

To map the modifiers, we began by generating F2 mutants. Intriguingly, while most of the mutants exhibited a severe phenotype with a survival of ~10 days, a small proportion lived to ~4 months indicating the presence of a potent modifier deriving from one or the other strain. Some of the mutants from the latter cohort survived beyond 12 months of age. A genome-wide linkage analysis of mice from the two SMA cohorts (mild and severe) uncovered a region on chromosome 9 of our C57Bl/mice that tightly associated with the less severe phenotype (FIG. 2). To ascertain whether a locus on this chromosome was responsible for mitigating the severe SMA phenotype, we created congenic SMA carriers deriving all except chromosome 9 from the FVB/N strain; chromosome 9 was derived from C57Bl/6. Based on a second genome-wide scan involving ~1500 polymorphic markers, we further narrowed the region of interest on chromosome 9 to a segment between 29 Mbp and 52 Mbp. This was later refined, based on recombinants, to a ~13 Mbp stretch of genomic sequence between the 39 Mbp and 52 Mbp region of chromosome 9.

Figure 3A:
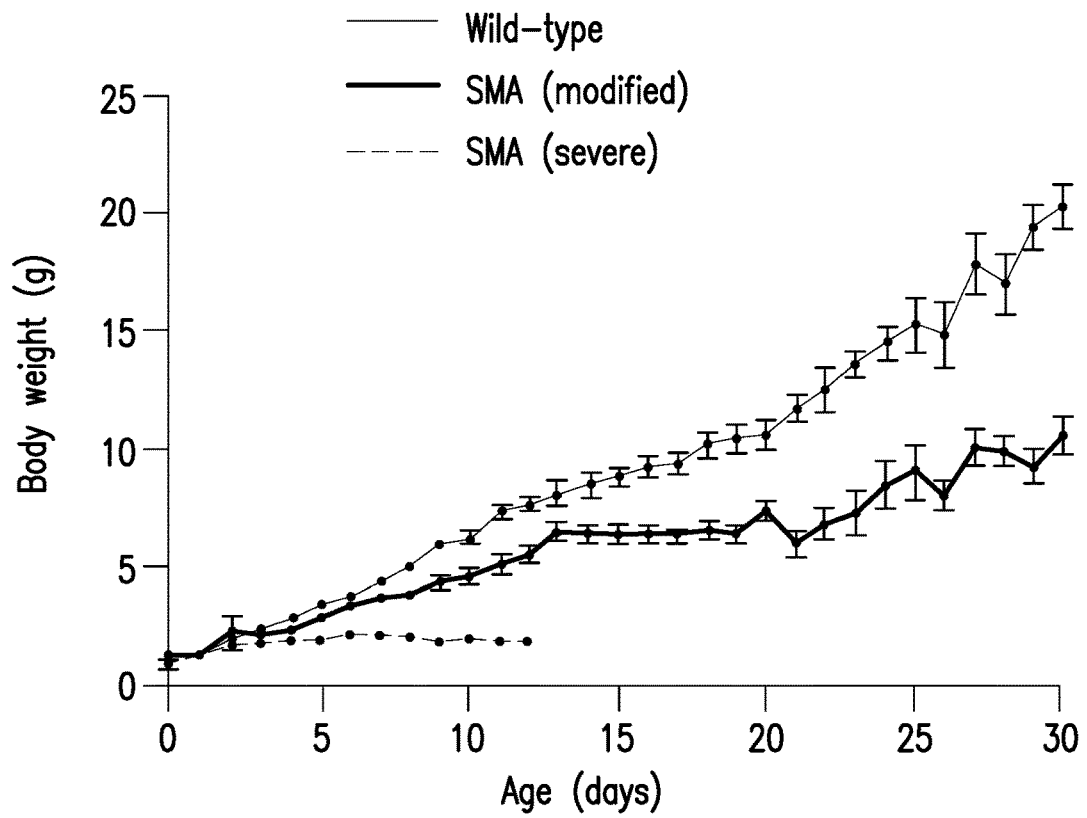
FIGS. 3A-3E. Suppression of the severe SMA phenotype in model mice. (A) Body weight curves of the modified SMA mutants and relevant controls (n≥20 mice of each cohort). (B) Kaplan-Meier curves depicting survival phenotypes in typically affected and modified F2 SMA model mice (n≥20 mice of each genotype). (C) Normal numbers of spinal motor neurons in modified SMA mutants. n≥3, t tests. (D) Spinal cord sections from modified SMA mutants and controls depicting vGlut1-positive sensory boutons abutting onto the motor neurons. (E) Graph depicting equivalence in numbers of sensory synapses on motor neurons of modified SMA mutants and controls. n≥3, t tests.
Figure 3B:
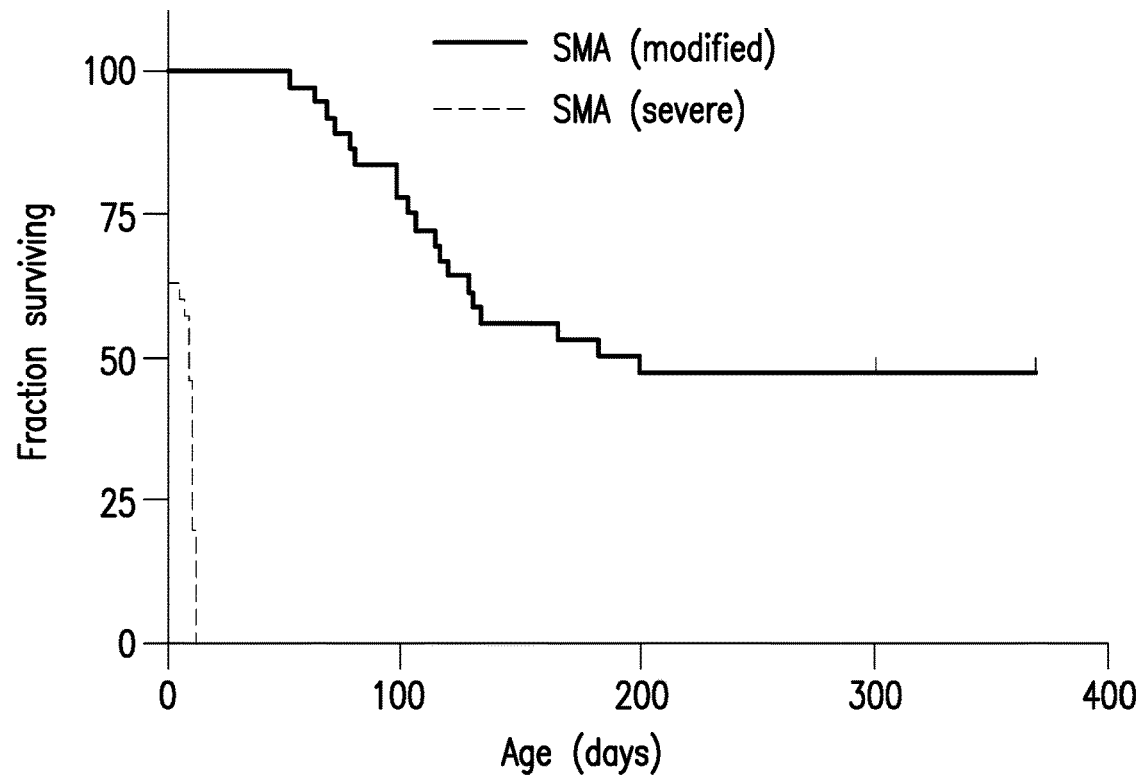
Figure 3C:
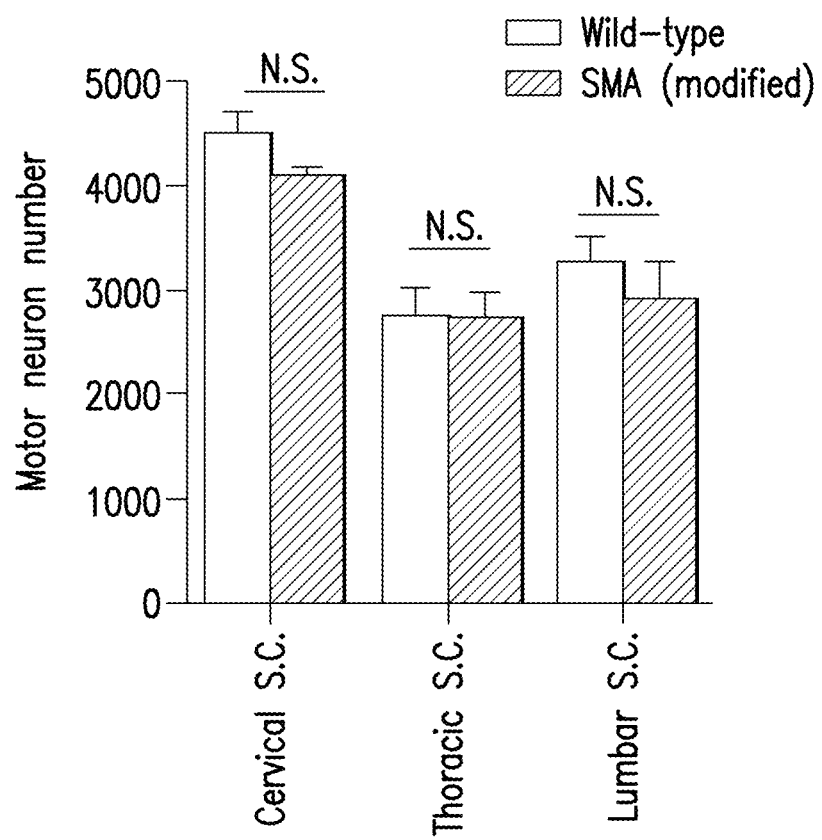
Figure 3D:
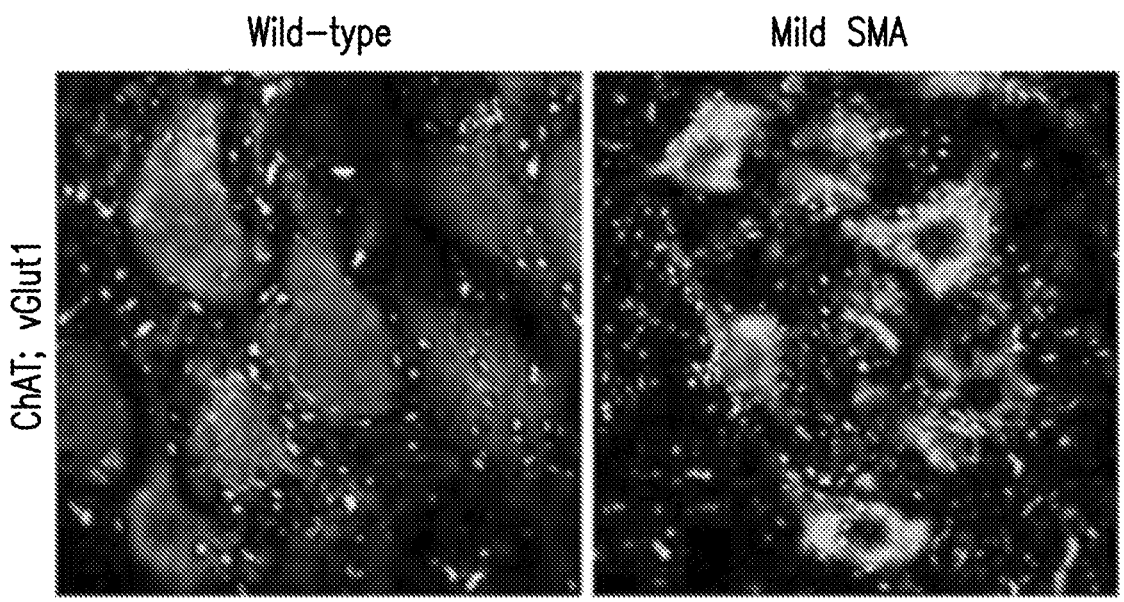
Figure 3E:
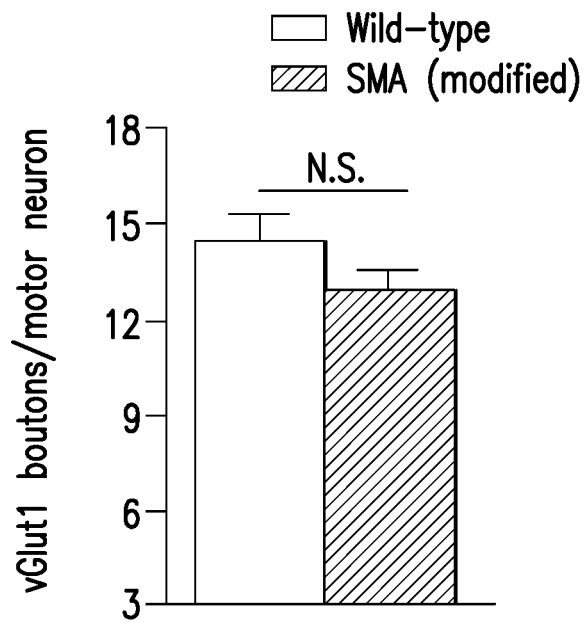

Whilst carrying out our analysis to identify the critical region of chromosome 9 harboring the SMA modifier, we pursued two additional lines of investigation. First, we conducted a detailed examination of our modified SMA mice. Second, we sequenced a cohort of typically affected SMA mice (survival of ~10 days) and compared the sequence to that of our modified mutants (survival of ~4 months). Typically affected SMA mice are significantly smaller than wild-type controls. In contrast, the modified mutants gained considerable weight during the first month of life and were markedly larger than their typically affected counterparts (FIG. 3A). Consistent with this finding, the modified mutants had a greatly extended lifespan relative to their typically affected littermates (FIG. 3B). A signature feature of SMA is the loss of spinal motor neurons. At 45 days of age, the modified mutants had normal numbers of these cells, suggesting that the modifier had prevented motor neuron degeneration (FIG. 3C). Moreover, sensory inputs onto the motor neurons, which are reduced in SMA, were restored in the modified mutants (FIGS. 3D, 3E). Finally, neurotransmission at the neuromuscular synapse, which is compromised in SMA, was found to be no different from WT controls in the modified mutants. These results indicate that the SMA modifier markedly, if not completely, rescues the neuromuscular disease phenotype so characteristic of the human disease.

We previously generated severely affected "SMND7" SMA model mice[25, 26]. These widely-used mutants model type 1 (severe) SMA in humans and succumb to disease at about 2 weeks of age. In the course of interbreeding carriers of this line of mice derived on the one hand on the pure FVB/N strain and on the other on the C57Bl/6 strain (FVB/N×C57Bl/6), we discovered that ~6% of the F2 SMA mutants—from an F1 cross—failed to develop the severe SMA phenotype, instead surviving beyond 1 year (FIG. 3B). This remarkable and spontaneous suppression of the early death phenotype characteristic of the SMND7 line of SMA model mice was accompanied by a significant increase in body weight (FIG. 3A) and a marked improvement in motor performance, deriving from enhanced muscle strength relative to that observed in typically affected mutants. Indeed, whereas typically affected mutants were essentially paralyzed by PND10, the milder, modified mutants achieved a righting ability score much closer to that of wild-type control littermates. By PND14, the mild mutants performed as well as the controls (Righting ability score in arbitrary units—Typical SMA mutants: 0.5±0.02; mild mutants: 5.7±0.25; wild-type: 6.0±0.5, n≥10, P>0.05 between mild mutants and controls, t test).

One of the most characteristic cellular phenotypes associated with SMA is a loss of 25-50% of the spinal MNs[5, 28]. Incredibly, at PND70, we found that the mild mutants exhibited no significant loss of these cells (FIG. 3C). Consistent with this finding, we determined that the numbers of sensory 1a afferents on the MNs, which are typically reduced in severe SMA mutants[29-31], were restored to normal in the mild mutants (FIGS. 3D, 3E). Peripheral MN defects, exemplified by severe morphological abnormalities of the neuromuscular junctions (NMJs), have been found to precede MN cell body loss in SMND7 SMA model mice[32]. Accordingly, we examined the NMJs of the mild mutants at PND70. In this case too, we failed to find evidence of any abnormalities. Pre-synaptic defects in the triceps, as assessed by NMJs with nerve terminals containing abnormal accumulations of neurofilament (NF) protein, did not differ appreciably between the mild mutants and controls (Mild mutants: 4.13±1.56 defective NMJs; wild-type: 3.26±1.33 defective NMJs, P=0.69, n≥300 NMJs from N=3 mice of each genotype, t test). Similarly, acetylcholine receptor (AChR) complexity, which is profoundly reduced in severe SMA mice, as assessed by NMJ perforations, appeared equivalent in mild mutants and wild-type controls (Number of NMJs with >3 perforations—Mild SMA mutants: 63±3.44; wild-type: 76±7.15, P=0.17 n≥300 NMJs from N=3 mice of each genotype, t test). These results suggest that in young adult mild SMA mutants, the neuromuscular disease phenotype is greatly mitigated, if not entirely ameliorated based on the specific outcomes described above.

We hypothesize that the G→R mutation in our mild SMA mutants is the critical mediator on chromosome 9 of the modified phenotype. Hspa8 has recently been implicated in synaptic microautophagy using *Drosophila* as a model system[36]. This process is important to neurotransmission, and mutations in Hspa8 can actually potentiate neurotransmitter release by increasing the readily releasable pool (RRP) of synaptic vesicles. Moreover, in SMA mutants, we and others have shown that evoked potentials and, consequently, neurotransmission is significantly depressed, likely due to a decrease in the RRP[32, 37, 38]. This depressed neurotransmission appears to be mitigated in mild SMA mutants. Our data support a role for Hspa8 in mediating the mild SMA phenotype.

An altered disease phenotype in transgenic model mice sometimes arises as a consequence of the gain or loss of underlying transgenes[33]. SMND7 SMA model mice harbor two transgenes—a genomic copy of the SMN2 gene and a cDNA expressing SMND7[25]. We used QPCR analysis to demonstrate that no gain in number of either transgene had occurred in the mild mutants. Congruent with this result, we found that the mild SMA mutants, like their severely affected counterparts, continued to express dramatically low levels of the SMN protein in nervous as well as non-nervous tissue. These aggregate findings provide compelling evidence of a remarkable mitigation of the SMA phenotype in mutants that typically exhibit an extremely aggressive form of the disease.

To demonstrate that the SMA-modifying mechanism associated with perturbations in Hspa8 involves the process of synaptic microautophagy, we have conducted or will conduct the following studies.

Experiment (Expt.) 1—Is Hspa8 a Bona Fide Mediator (Suppressor) of the Severe SMA Phenotype in SMND7 Model Mice?

Expt. 1A: Introducing the Hspa8$^{G470R}$ missense mutation into the SMA background. Every mildly affected SMND7 SMA mutant generated since the inception of this study (n>100), without exception, was determined to be homozygous for the Hspa8$^{G470R}$ mutation. To show that the mutant Hspa8 is sufficient to recapitulate the mild SMA phenotype, we have introduced this mutation into SMND7 mutants that derive the rest of their genomes from the FVB/N strain of mice.

Figure 4:
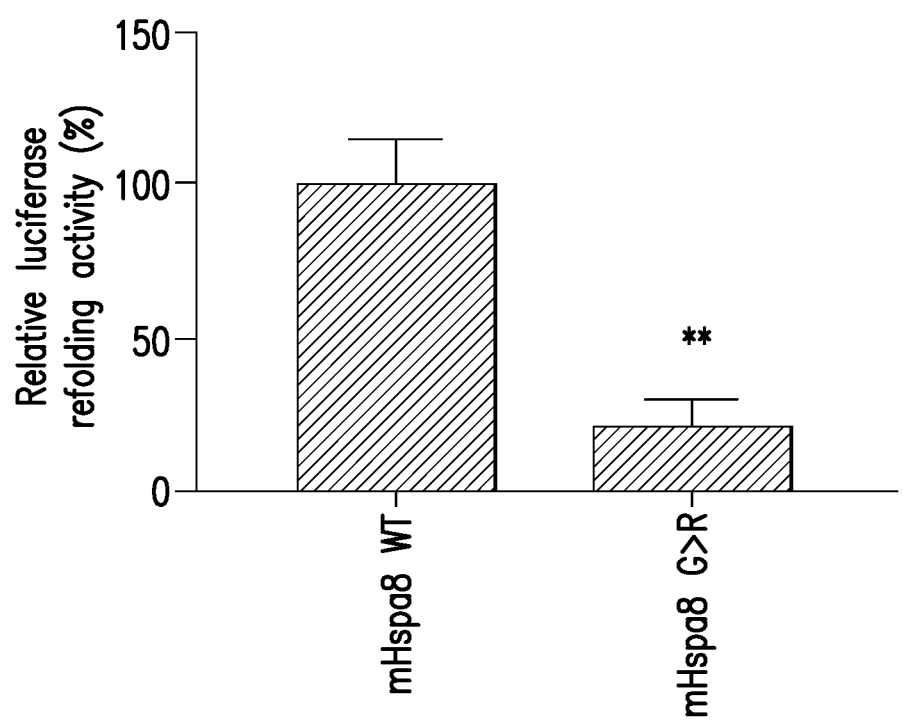
FIG. 4. Mutant Hspa8 is less efficient as a chaperone as measured in the luciferase refolding assay suggesting that its activity is shifted toward synaptic microauto-phagy.

The results of our sequencing data uncovered two putative missense mutations in the ~13 Mbp region of chromosome 9 of our modified SMA mutants. The first, in the δ-COP gene, was found to stem from a pseudogene at a different chromosomal locus and was quickly ruled out as a candidate modifier. The second, a G470R mutation in the Hspa8 gene, was further investigated by introducing it onto the typically affected SMA background using standard knock-in technology. Our results indicate that this mutation is indeed our modifier of interest. SMA mutants carrying the G470R change in the Hspa8 exhibit an improved motor performance and a significantly extended lifespan. In other studies, mutations in Hspa8 have been shown to improve neurotransmission by enhancing synaptic microautophagy. Experiments to investigate if the mechanism through which the G470R mutation suppresses the SMA phenotype involves synaptic microautophagy indicates that this is indeed the case (FIG. 4). The mutation lowers the chaperone activity of the protein, shifting the function of Hspa8 toward synaptic microautophagy. This is consistent with our in vivo findings in which neurotransmission was found to be normal in the modified mutants.

Expt. 1B: Is the Hspa8$^{G470R}$ mutation sufficient to mediate the mild phenotype in typically severe SMND7 mutant mice? Once we have identified potential founders, we will establish crosses to generate SMA mice homozygous for mutant Hspa8, heterozygous for the mutation or wild-type at the locus. We will then characterize the mutants using a comprehensive battery of molecular, cellular and behavioral assays which are described in greater detail below.

Phenotyping Assays—The three cohorts of SMA mutants and wild-type controls will be weighed daily from birth until PND18 and, if necessary, weekly thereafter. Peak weight will be recorded in each instance. Secondly, we will assess survival in the mice. This simple but disease-relevant assay will be plotted as Kaplan-Meier survival curves and statistically evaluated for differences between the various groups of mice using the log-rank test. Thirdly, we will subject the animals to two tests of muscle strength, the righting reflex assay administered daily between PND2 and PND8, and the hanging tube test administered on PND5, 6 and 7 (refs. 41, 42). The former test measures abdominal and trunk muscle integrity; the latter assesses hind-limb strength. Finally, in instances when survival is substantially enhanced, we will pay close attention to gross phenotype, including ability to groom and breed. We will compare, whenever possible, the outcomes obtained in our knock-in mice to those established in mutants carrying the ~4 Mbp and/or ~19 Mbp ROI that was identified in our mapping studies. Results from our single Hspa8$^{G470R}$ line of mice support the notion that the missense mutation is our suppressor; crosses established using SMA carriers heterozygous for G470R have thus far yielded ~6 SMA mice harboring one G470R mutant allele and 1 SMA mouse homozygous for the mutation. In each instance, survival relative to that of typically affected SMND7 SMA mice was markedly enhanced (SMA:: G470R$^{+/+}$=45 days; SMA::G470R$^{+/-}$=19.7±3 days; SMA:: G470R$^{-/-}$=10±2.5 days, P<0.004 log-rank test between the latter two cohorts, n≥6).

Neuromuscular Pathology—Spinal MN loss and skeletal muscle atrophy are defining attributes of the SMA phenotype. Accordingly, each of these attributes will be investigated in the mutants with or without the G470R mutation. Spinal MNs will be quantified at lumbar, thoracic and cervical levels, and muscle atrophy examined in both the relatively resistant gastrocnemius as well as the more vulnerable triceps and splenius muscles. Given the widespread NMJ defects of SMA mice, we will also pay close attention to the effects of mutant Hspa8 on SMA synapses. Nerve terminals, which are poorly arborized in SMA mutants, will be examined immunohistochemically using antibodies against NF protein and synaptophysin. The size, complexity and staining intensity of the post-synaptic AChRs will be determined following immuno-labeling with fluorescent a-bungarotoxin. In parallel, we will make certain to quantify any evidence of denervation by examining the extent to which pre-and post-synapses are in perfect register. Finally, since the neuromuscular pathology that we and others have observed is reflected in reduced neurotransmission, we will also carry out electrophysiological recordings in the semitendinosus NMJs of mutants with or without mutant Hspa8. mEPPs, EPPs, quantal content and the ability of junctions to respond appropriately to repetitive stimulation will be assessed (also see Expt. 2). We will conduct them as reported earlier[29, 32].

RNA and Protein Studies—The best-known modulator of the SMA phenotype is the copy gene, SMN2. A gain in SMN2 copy number or processes that induce it to express higher levels of the FL-SMN transcript and thus higher levels of SMN protein reliably mitigate the SMA phenotype. Accordingly, we will examine SMN transcript as well as protein levels in the SMA mutants with or without the G470R lesion. FL-SMN as well as SMND7 transcripts from SMN2 will be evaluated and an assessment of their absolute levels and relative ratios (FL-SMN:SMND7) used to determine if and how SMN2 gene transcription might be modulated by mutant Hspa8. These studies will be complemented with western blot experiments and, if necessary, quantitative ELISA assays to assess SMN protein levels. RNA and protein levels will be determined in a variety of tissues from PND7 mice, revealing whether and precisely how (transcriptional/post-transcriptional; SMN-dependent/SMN-independent) the severe SMA phenotype is mitigated in mutants harboring the mutant Hspa8 gene. These experiments may be particularly informative given one report in which SMN was found to interact with Hspa8[43].

While an examination of SMN levels in the SMA mutants is critical to explaining the mild phenotype we have identified, we will also assess the effects of the G470R mutation on Hspa8 levels in the mice. QPCR will be used to assess Hspa8 transcript levels; western blots will suffice to quantify mutant protein levels. Studies on tissue of mild SMA mice on the mixed (C57×FVB) background suggest that the mutant Hspa8 and wild-type proteins are expressed at equivalent levels. We will extend this result in a variety of tissues from SMA mutants harboring the Hspa8$^{G470R}$ knockin. Assessments will be made at time points similar to those proposed for examining SMN levels.

Behavioral studies will employ n≥15 based on detecting an effect size of at least 30% using t tests for independent samples with common variances at a=0.05 and power (1-b) ≥0.8 (StatMate, GraphPad). To assess SMN and Hspa8 expression in the mice, sample sizes of n≥5 will be deemed sufficient based on similar power analysis calculations. Mice of both genders will be used, but results reported separately for the two. Appropriate controls will be gender and age-matched littermates. Statistical tests employed for comparisons of means will include t tests and ANOVA with post-hoc analyses. Longitudinal data e.g., weight curves will be analyzed using the Statmod statistical package[44].

Expt. 2—Does Improved Microautophagy at the Neuromuscular Synapse Link the Hspa8$^{G470R}$ Mutation to a Mitigation of the SMA Phenotype?

Hspa8 is perhaps best recognized for facilitating the proper folding of newly translated or misfolded proteins and thus as a chaperone that ensures quality control of polypeptides[45]. However, its role in cellular proteostasis is effected in more ways than one. One recent discovery suggests that it plays a critical role in synaptic microautophagy—the process of disassembling damaged and dysfunctional proteins in endosomes/lysosomes into their constituent parts for eventual re-use[46]. In *Drosophila* such a mechanism for turning over proteins is indispensable for ensuring proper neurotransmission at the NMJ, and critically dependent upon proper Hspa8 function[36]. We suggest that Hspa8 modulates the effects of low SMN through this process; the G470R mutant version of the protein potentiates microautophagy and restores normal neurotransmission at the NMJ. In this regard, it is important to note that Hspa8 is one of the most abundant synaptic proteins[47].

Expt. 2A: Does the G470R mutation affect Hspa8 chaperone activity? There is a fine balance between the chaperone activity of Hspa8, which involves ATP and the co-chaperone proteins Sgt (small glutamate-rich tetratricopeptide repeat-containing protein) and CSP (cysteine string protein), and its role in microautophagy, which is effected independently of ATP and the co-chaperones[36]. Altering the ratio of Hspa8 with respect to its co-chaperones, or introducing mutations in certain Hspa8 domains, can shift the balance towards or away from microautophagy and thus alter neurotransmission at the NMJ. For instance, mutations in the ATPase domain disrupt chaperone activity but leave the role of Hspa8 in microautophagy intact. In contrast, mutations in the C-terminal domain of Hspa8, which mediate the interaction of the protein with the lysosomal/endosomal membrane, abolish microautophagy but fail to affect the ability of the protein to refold proteins (chaperone activity). We suggest that the G470R mutation, which lies in the substrate binding domain, essential for chaperone activity, perturbs the ability of Hspa8 to refold proteins, shifting activity towards microautophagy. To test this, we will examine the ability of Hspa8$^{G470R}$ to refold luciferase. Briefly, recombinant luciferase (QuantiLum Recombinant Luciferase, Promega) will be diluted in refolding buffer, denatured and then mixed with purified Hspa8$^{G470R}$, CSP and Sgt. The bioluminescence from the luciferase will be assayed, following the addition of Luciferase Assay reagent (Promega), at regular intervals in a luminometer or plate reader. Controls will include wild-type Hspa8 and an ATPase-dead mutant, Hspa8$^{D10N}$ (ref. 48), known to disrupt chaperone activity. We tested the chaperone activity of crude yeast lysate from cells transfected with either an Hspa8$^{G470R}$ or WT construct. Lysate containing the mutant protein is only a third as efficient as lysate containing WT Hspa8 (FIG. 4). We will extend this finding using purified proteins.

Expt. 2B: Does the G470R mutation affect Hspa8-dependent microautophagy? Hspa8-dependent microautophagy relies on the ability of the protein to bind the lysosomal/endosomal membrane. In so doing, Hspa8 deforms the membrane to form tubules, a phenomenon that can be quantified using a "tubulation" assay[36]. Unlike its presumed defective chaperone activity, we suggest that Hspa8$^{G470R}$ deforms membranes and therefore drives microautophagy as robustly as wild-type protein. To test this, we will subject the two proteins and a control, Hspa8$^{3KA}$, that fails to deform membranes[36], to the tubulation assay. Essentially, bacterial lysate from *E. coli* over-expressing the different Hspa8 molecules will be combined with fluorescently labeled giant unilamellar vesicles (GUVs) made from a defined mixture of lipids that roughly mimic synaptic membranes[49], and the ability of the proteins to trigger membrane deformation/tubule formation will be assessed by fluorescence microscopy. To complement these in vitro experiments, we will assess the ability of Hspa8$^{G470R}$ protein to deform membranes in vivo. For this, the protein and relevant controls will be separately expressed in *S. cerevisae* and vacuolar membrane invagination and intraluminal vesicle formation determined using a co-expressed Vba1-GFP construct as a marker[50]. An in vivo study employing the WT and Hspa8$^{G470R}$ proteins suggests that the mutant is indeed competent in this microautophagy assay.

Expt. 2C: Testing the effects of Hspa8$^{G470R}$ on synaptic protein levels. Hspa8-mediated synaptic microautophagy depends on a pentapeptide motif on client proteins biochemically related to the sequence, KFERQ[51]. Roughly 53% of 170 synaptic proteins harbor at least one such microautophagy recognition motif[47] (MRM) which is bound by Hspa8 before the target protein is delivered to the lysosome/endosome. In Hspa8 mutants that are unable or inefficient at effecting microautophagy, the levels of synaptic proteins with MRMs rise as damaged/dysfunctional molecules accumulate; repletion of wild-type Hspa8 restores the levels of the proteins to those constituting just the functional pool[36]. We will test the effect of the Hspa8$^{G470R}$ mutation on microautophagy by assessing levels of at least 4 synaptic proteins (Bassoon, Piccolo, Munc13a and Synaptojanin) that harbor at least one MRM and are reportedly important for neurotransmission, and an equal number of synaptic proteins (Synaptophysin, a-SNAP, Complexin1 and Synaptotagmin1) devoid of an MRM. Levels of the protein will be detected immunocyto-chemically at NMJs of PND7 SMA mice (n≥5) with or without the G470R mutation. In addition to including wild-type (Smn$^{+/+}$) control animals, we will include animals administered an AAV9-delivered shRNA against Hspa8. The shRNA is expected to knock down levels of the protein, concomitantly increasing levels of the synaptic proteins harboring the MRM. We predict that the levels of the synaptic proteins with the MRMs will increase in SMA;Hspa8$^{WT}$ mutants but be restored to normal in SMA; Hspa8$^{G470R}$ mutants. In contrast, levels of the synaptic proteins devoid of the MRMs will remain identical in the two cohorts of SMA mutants and mice knocked down for Hspa8.

Figure 5A:
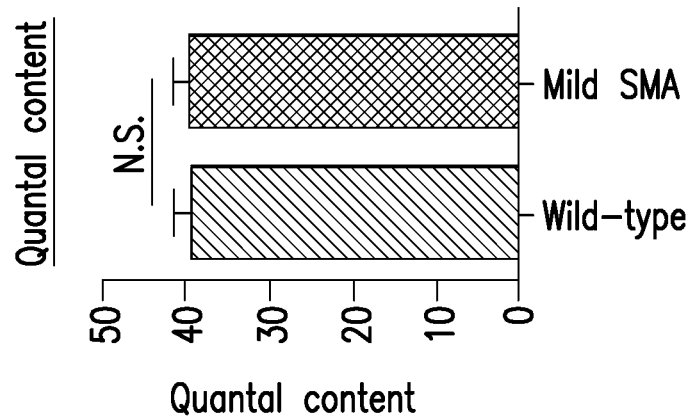
FIGS. 5A-5C. NMJ electrophysiology in mild SMA mutants. (A) miniature end-plate potentials (mEPPs), (B) end-plate potentials (EPPs) and (C) Quantal content were all found to be restored in mixed (C57×FVB) SMA mice homozygous for a region of chromosome 9 harboring the Hspa8G470R mutation. Note: Wild-type denotes mice wild-type at the Smn locus. N=3 of each cohort; t test.
Figure 5B:
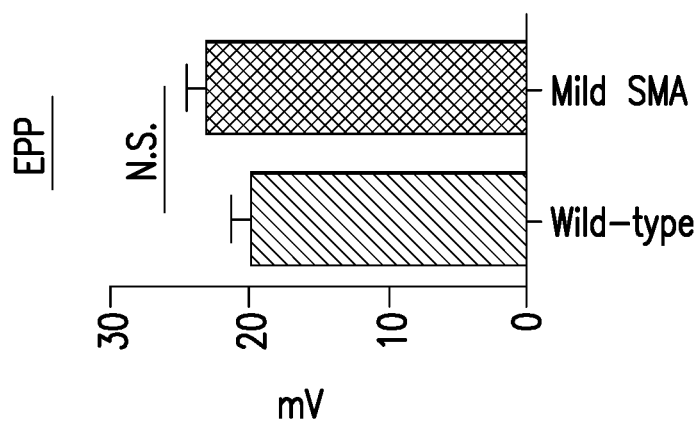
Figure 5C:
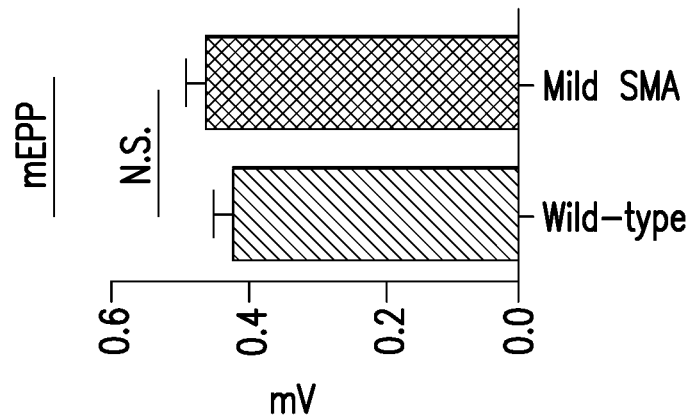

Expt. 2D: Does the Hspa8$^{G470R}$ mutation mitigate neurotransmission defects in SMND7 SMA mutants? Defects in Hspa8-mediated microautophagy depress neurotransmission whereas potentiating microautophagy either by over-expressing wild-type Hspa8 or by tuning down the chaperone activity of the protein restores neurotransmitter release at the NMJ[36]. This restored neurotransmission is facilitated through a normalization/increase in the RRP of synaptic vesicles. We will electrophysiologically examine the effects of the Hspa8$^{G470R}$ mutation on neurotransmission in SMA mice. We and others have previously shown that neurotransmission is significantly impaired in typically affected SMND7 SMA model mice[32, 37, 38]. This derives, at least in part, from a diminution of the RRP as well as a decreased probability of release[37]. We will examine a multitude of electrophysiological parameters as surrogates of neurotransmission in our SMA mice. mEPPs, EPPs, quantal content and facilitation will all be examined in the semitendinosus muscle of PND14 SMA mice (n≥5) with or without the Hspa8$^{G470R}$ mutation. To calculate the size of the RRP, we will plot quantal content of individual responses following repetitive stimulation (20 Hz, 5 sec) against accumulated quantal content and then draw a straight line through the declining phase of the response to the x-axis. Release probability will be calculated by dividing the quantal content obtained from the first EPP by the RRP size. To complement these studies with morphological data, we will consider electron microscopy analysis of individual NMJs in the muscle. This type of analysis[32] will enable us to visualize the number of vesicles at NMJs, and if the vesicles are docked for neurotransmitter release or not. Of particular relevance to the electrophysiological experiments proposed here, we have already shown, albeit in mixed background mild, PND70 SMND7 SMA mice, that there is a considerable mitigation of neurotransmission defects (FIGS. 5A-5C).

Our data suggest that mutant Hspa8 is a mediator of the SMA phenotype, acting through its role in synaptic microautophagy to potentiate neurotransmission at the NMJ and thus mitigate disease. Successfully demonstrating this will focus attention on a novel mechanism in SMA-SMN-mediated proteostasis at the synapse, sparking interest in how wild-type SMN levels maintain a healthy pool of NMJ proteins that ensure that the synapse functions efficiently to signal between nerve and muscle.

To test whether Hspa8$^{G470R}$ functions through mechanisms other than microautophagy, we will examine the role of the mutation in endocytosis, another process thought to be perturbed at SMA junctions[64, 65].

Postnatal day (PND) 1 mouse pups (n=3 for each time point analyzed) were administered, through the retro-orbital sinus, either vehicle or 10 µl of 4×10$^{11}$ GC (genome copies)

Figure 6A:
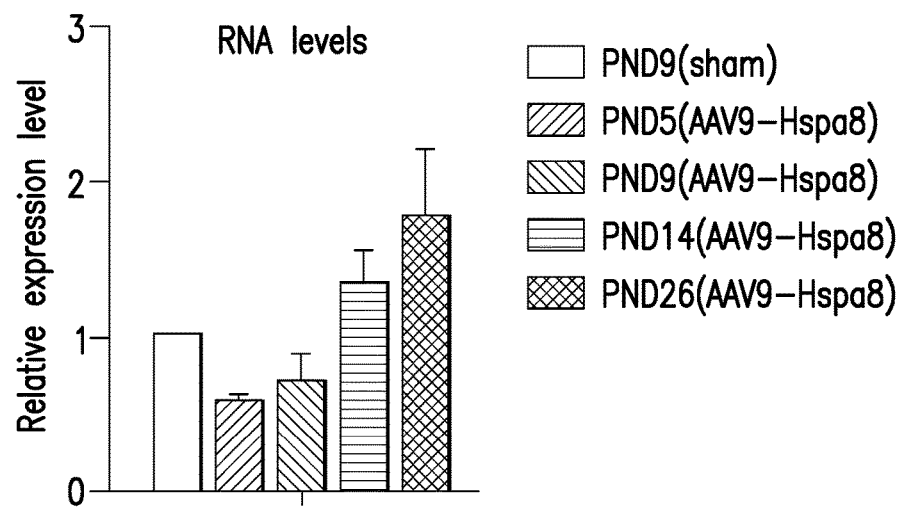
FIGS. 6A-6C. Evidence of successful delivery and expression of therapeutic Hspa8. (A) Hspa8 transcript levels increase following delivery of the molecule in AAV9 to model mice. (B) A corresponding increase of the protein is seen. (C) Western blot of therapeutic Hspa8 showing robust increase in the protein in PND14 and PND26 mice above baseline.
Figure 6B:
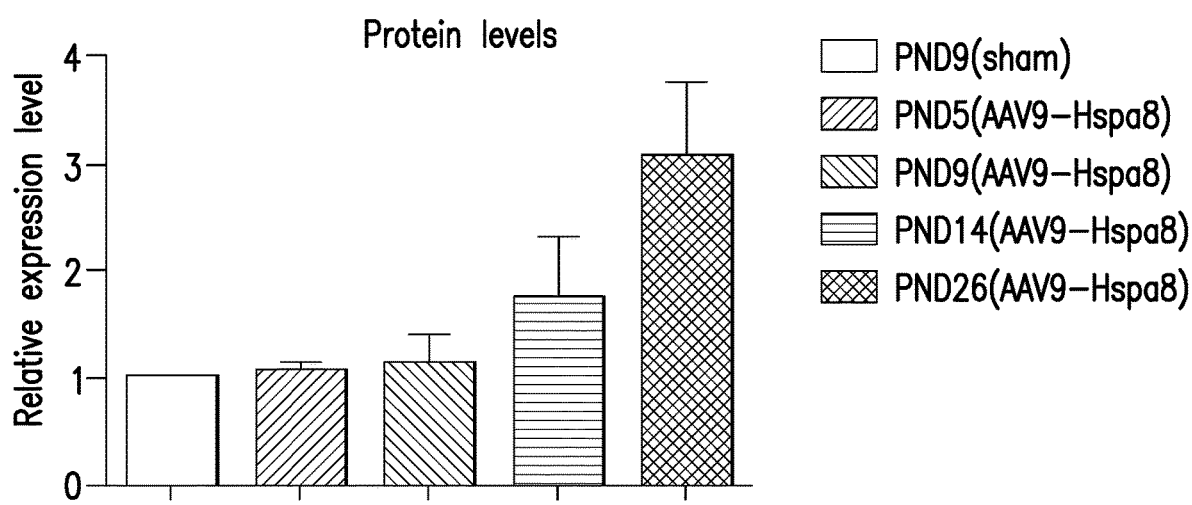
Figure 6C:
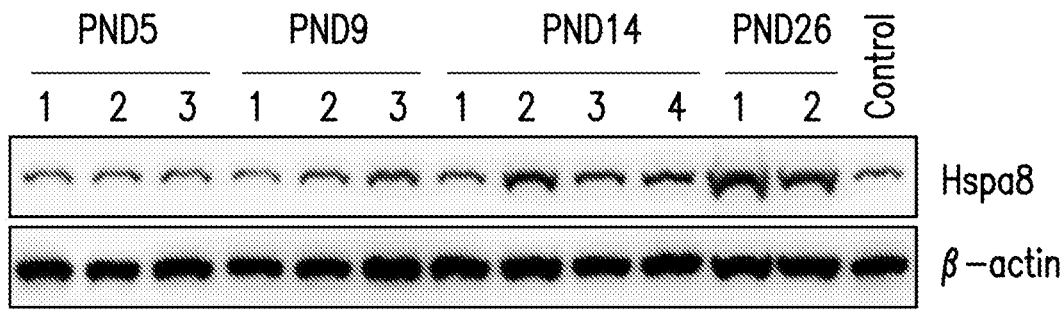

(concentration is about 4×10¹³ GC/ml) of the AAV9-Hspa8 therapeutic construct (AAV9-Hspa8$^{G470R}$). Following the injection, the pups were euthanized at PND5, PND9, PND14 or PND26, and brain tissue extracted to assess total levels of Hspa8 transcript and/or protein (including both wildtype Hspa8 and Hspa8$^{G470R}$). Transcript levels were assessed by Q-PCR on an Eppendorf RealPlex 4 MasterCycler. Protein levels were determined by standard western blot analysis using β-tubulin as a loading control. Band intensities were determined using the NIH ImageJ software. FIGS. 6A-6C show evidence of successful delivery and expression of therapeutic Hspa8. Hspa8 transcript levels increase following delivery of the molecule in AAV9 to model mice (FIG. 6A). A corresponding increase of the protein is seen (FIG. 6B). Western blot of Hspa8 shows robust increase in the protein in PND14 and PND26 mice above baseline (FIG. 6C).

Figure 7:
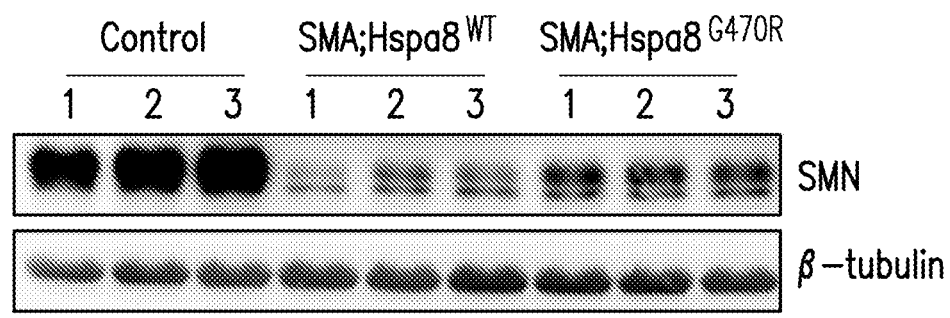
FIG. 7. The therapeutic version of Hspa8 increases SMN in spinal cord tissue of SMA mice as assessed by western blot analysis.

PND10 mice of the indicated genotypes were euthanized, and the spinal cord tissue extracted to determine SMN levels by western blotting. β-tubulin was used as a loading control. Band intensities were determined using the NIH ImageJ software. FIG. 7 shows that the therapeutic version of Hspa8 increases SMN in spinal cord tissue of SMA mice as assessed by western blot analysis.

REFERENCES

1. Lefebvre S, Bürglen L, Reboullet S, Clermont O, Burlet P, Viollet L, Benichou B, Cruaud C, Millasseau P, Zeviani M, et al (1995) Identification and characterization of a spinal muscular atrophy-determining gene. *Cell.* 80:155-65.
2. Lefebvre, S., Burlet, P., Liu, Q., Bertrandy, S., Clermont, O., Munnich, A., Dreyfuss, G. and Melki, J. (1997) Correlation between severity and SMN protein level in spinal muscular atrophy. *Nat. Genet.* 16: 265-69.
3. Coovert D D, Le T T, McAndrew P E, Strasswimmer J, Crawford T O, Mendell J R, Coulson S E, Androphy E J, Prior T W, Burghes A H (1997) The survival motor neuron protein in spinal muscular atrophy. *Hum Mol Genet.* 8:1205-14.
4. Rochette C F, Gilbert N, Simard L R (2001) SMN gene duplication and the emergence of the SMN2 gene occurred in distinct hominids: SMN2 is unique to *Homo sapiens*. *Hum Genet.* 108:255-66.
5. Monani, U R (2005) Spinal muscular atrophy: a deficiency in a ubiquitous protein; a motor neuron-specific disease. *Neuron.* 48:885-96.
6. Monani U R, Lorson C L, Parsons D W, Prior T W, Androphy E J, Burghes A H, McPherson J D (1999) A single nucleotide difference that alters splicing patterns distinguishes the SMA gene SMN1 from the copy gene SMN2. *Hum Mol Genet.* 7:1177-83.
7. Lorson C L, Hahnen E, Androphy E J, Wirth B (1999) A single nucleotide in the SMN gene regulates splicing and is responsible for spinal muscular atrophy. *Proc Natl Acad Sci USA.* 96:6307-11.
8. Singh N K, Singh N N, Androphy E J, Singh R N (2006) Splicing of a critical exon of human Survival Motor Neuron is regulated by a unique silencer element located in the last intron. *Mol Cell Biol.* 26:1333-46.
9. Hua Y, Vickers T A, Baker B F, Bennett C F, Krainer A R (2007) Enhancement of SMN2 exon 7 inclusion by antisense oligonucleotides targeting the exon. *PLoS Biol.* 5:e73.
10. Hua Y, Vickers T A, Okunola H L, Bennett C F, Krainer A R. (2008) Antisense masking of an hnRNP A1/A2 intronic splicing silencer corrects SMN2 splicing in transgenic mice. *Am J Hum Genet.* 82:834-48.
11. Porensky P N, Mitrpant C, McGovern V L, Bevan A K, Foust K D, Kaspar B K, Wilton S D, Burghes A H. (2012) A single administration of morpholino antisense oligomer rescues spinal muscular atrophy in mouse. *Hum Mol Genet.* 21:1625-1638
12. d'Ydewalle C, Sumner C J (2015) Spinal Muscular Atrophy Therapeutics: Where do we Stand? *Neurotherapeutics.* 12:303-16
13. Pellizzoni L (2007) Chaperoning ribonucleoprotein biogenesis in health and disease. *EMBO Rep.* 8:340-5.
14. Chari A, Paknia E, Fischer U. (2009) The role of RNP biogenesis in spinal muscular atrophy. *Curr Opin Cell Biol.* 2:387-93.
15. Schrank B, Götz R, Gunnersen J M, Ure J M, Toyka K V, Smith A G, Sendtner M (1997) Inactivation of the survival motor neuron gene, a candidate gene for human spinal muscular atrophy, leads to massive cell death in early mouse embryos. *Proc Natl Acad Sci USA.* 94:9920-5.
16. Monani U R, De Vivo D C. Neurodegeneration in spinal muscular atrophy: from disease mechanism and animal models to therapeutic strategies and beyond. *Future Neurol.* 9:49-65.
17. Cifuentes-Diaz C, Frugier T, Tiziano F D, Lacène E, Roblot N, Joshi V, Moreau M H, Melki J (2001) Deletion of murine SMN exon 7 directed to skeletal muscle leads to severe muscular dystrophy. *J Cell Biol.* 152:1107-14.
18. Gavrilina T O, McGovern V L, Workman E, Crawford T O, Gogliotti R G, DiDonato C J, Monani U R, Morris G E, Burghes A H. (2008) Neuronal SMN expression corrects spinal muscular atrophy in severe SMA mice while muscle-specific SMN expression has no phenotypic effect. *Hum Mol Genet.* 17:1063-75.
19. Iyer C C, McGovern V L, Murray J D, Gombash S E, Zaworski P G, Foust K D, Janssen P M, Burghes A H. (2015) Low levels of Survival Motor Neuron protein are sufficient for normal muscle function in the SMNΔ7 mouse model of SMA. *Hum Mol Genet.* 24:6160-73.
20. Hayhurst M, Wagner A K, Cerletti M, Wagers A J, Rubin L L (2012) A cell-autonomous defect in skeletal muscle satellite cells expressing low levels of survival of motor neuron protein. *Dev Biol.* 368:323-34.
21. Boyer J G, Murray L M, Scott K, De Repentigny Y, Renaud J M, Kothary R (2013) Early onset muscle weakness and disruption of muscle proteins in mouse models of spinal muscular atrophy. *Skelet Muscle.* 3:24
22. Martinez T L, Kong L, Wang X, Osborne M A, Crowder M E, Van Meerbeke J P, Xu X, Davis C, Wooley J, Goldhamer D J, Lutz C M, Rich M M, Sumner C J. (2012) Survival motor neuron protein in motor neurons determines synaptic integrity in spinal muscular atrophy. *J Neurosci.* 32:8703-15
23. Buchner D A, Trudeau M, Meisler M H. (2003) SCNM1, a putative RNA splicing factor that modifies disease severity in mice. *Science.* 30:967-9.
24. Nadeau J H (2003) Modifier genes and protective alleles in humans and mice. *Curr Opin Genet Dev.* 13:290-5.
25. Le T T, Pham L T, Butchbach M E, Zhang H L, Monani U R, Coovert D D, Gavrilina T O, Xing L, Bassell G J, Burghes A H (2005) SMNDelta7, the major product of the centromeric survival motor neuron (SMN2) gene, extends survival in mice with spinal muscular atrophy and associates with full-length SMN. *Hum Mol Genet.* 14:845-57
26. Monani U R, Sendtner M, Coovert D D, Parsons D W, Andreassi C, Le T T, Jablonka S, Schrank B, Rossoll W, Prior T W, Morris G E, Burghes A H (2000) The human centromeric survival motor neuron gene (SMN2) rescues embryonic lethality in Smn(−/−) mice and results in a mouse with spinal muscular atrophy. *Hum Mol Genet.* 9:333-9

27. Miniou P, Tiziano D, Frugier T, Roblot N, Le Meur M, Melki J (1999) Gene targeting restricted to mouse striated muscle lineage. *Nucleic Acids Res.* 27:e27.

28. Burghes A H and Beattie C E (2009) Spinal muscular atrophy: why do low levels of survival motor neuron protein make motor neurons sick? *Nat Rev Neurosci.* 10:597-609.

29. Park G H, Maeno-Hikichi Y, Awano T, Landmesser L T, Monani U R (2010) Reduced survival of motor neuron (SMN) protein in motor neuronal progenitors functions cell autonomously to cause spinal muscular atrophy in model mice expressing the human centromeric (SMN2) gene. *J Neurosci.* 30:12005-19

30. Ling K K, Lin M Y, Zingg B, Feng Z, Ko C P (2010) Synaptic defects in the spinal and neuromuscular circuitry in a mouse model of spinal muscular atrophy. *PLoS One* 5:e15457

31. Mentis G Z, Blivis D, Liu W, Drobac E, Crowder M E, Kong L, Alvarez F J, Sumner C J, O'Donovan M J (2011) Early functional impairment of sensory-motor connectivity in a mouse model of spinal muscular atrophy. *Neuron.* 69:453-67

32. Kariya S, Park G H, Maeno-Hikichi Y, Leykekhman O, Lutz C, Arkovitz M S, Landmesser L T, Monani U R (2008) Reduced SMN protein impairs maturation of the neuromuscular junctions in mouse models of spinal muscular atrophy. *Hum Mol Genet.* 17:2552-69

33. Heiman-Patterson T D, Sher R B, Blankenhorn E A, Alexander G, Deitch J S, Kunst C B, Maragakis N, Cox G (2011) Effect of genetic background on phenotype variability in transgenic mouse models of amyotrophic lateral sclerosis: a window of opportunity in the search for genetic modifiers. *Amyotroph Lateral Scler.* 12:79-86.

34. Li H, Custer S K, Gilson T, Hao le T, Beattie C E, Androphy E J. (2015) α-COP binding to the survival motor neuron protein SMN is required for neuronal process outgrowth. *Hum Mol Genet.* 24:7295-307.

35. Custer S K, Gilson T D, Li H, Todd A G, Astroski J W, Lin H, Liu Y, Androphy E J. (2016) Altered mRNA Splicing in SMN-Depleted Motor Neuron-Like Cells. *PLoS One.* 11:e0163954.

36. Uytterhoeven V, Lauwers E, Maes I, Miskiewicz K, Melo M N, Swerts J, Kuenen S, Wittocx R, Corthout N, Marrink S J, Munck S, Verstreken P. (2015) Hsc70-4 Deforms Membranes to Promote Synaptic Protein Turnover by Endosomal Microautophagy. *Neuron.* 88:735-48.

37. Torres-Benito L, Neher M F, Cano R, Ruiz R, Tabares L. (2011) SMN requirement for synaptic vesicle, active zone and microtubule postnatal organization in motor nerve terminals. *PLoS One.* 6:e26164.

38. Kong L, Wang X, Choe D W, Polley M, Burnett B G, Bosch-Marcé M, Griffin J W, Rich M M, Sumner C J (2009) Impaired synaptic vesicle release and immaturity of neuromuscular junctions in spinal muscular atrophy mice. *J Neurosci.* 29:842-51

39. Lotti F, Imlach W L, Saieva L, Beck E S, Hao le T, Li D K, Jiao W, Mentis G Z, Beattie C E, McCabe B D, Pellizzoni L (2012) An SMN-dependent U12 splicing event essential for motor circuit function. *Cell.* 151:440-54

40. Singh P, Schimenti J C, Bolcun-Filas E (2015) A mouse geneticist's practical guide to CRISPR applications. *Genetics.* 199:1-15.

41. Butchbach M E, Edwards J D, Burghes A H (2007) Abnormal motor phenotype in the SMNDelta7 mouse model of spinal muscular atrophy. *Neurobiol Dis.* 27:207-19

42. El-Khodor B F, Edgar N, Chen A, Winberg M L, Joyce C, Brunner D, Suárez-Fariñas M, Heyes M P (2008) Identification of a battery of tests for drug candidate evaluation in the SMNDelta7 neonate model of spinal muscular atrophy. *Exp Neurol.* 212:29-43

43. Meister G, Bühler D, Pillai R, Lottspeich F, Fischer U. (2001) A multiprotein complex mediates the ATP-dependent assembly of spliceosomal U snRNPs. *Nat Cell Biol* 3:945-9

44. Elso C M, Roberts L J, Smyth G K, Thomson R J, Baldwin T M, Foote S J and Handman E. (2004) Leishmaniasis host response loci (lmr13) modify disease severity through a Th1/Th2-independent pathway. *Genes Immunity* 5:93-100

45. Liu T, Daniels C K, Cao S (2012) Comprehensive review on the HSC70 functions, interactions with related molecules and involvement in clinical diseases and therapeutic potential. *Pharmacol Ther.* 136:354-74.

46. McPherson P. S. (2015) Eating Locally: Microautophagy and Protein Turnover at the Synapse. *Neuron.* 88:619-21.

47. Wilhelm B G, Mandad S, Truckenbrodt S, Kröhnert K, Schäfer C, Rammner B, Koo S J, Claßen G A, Krauss M, Haucke V, Urlaub H, Rizzoli S O. (2014) Composition of isolated synaptic boutons reveals the amounts of vesicle trafficking proteins. *Science.* 344:1023-8.

48. Huang S P, Tsai M Y, Tzou Y M, Wu W G, Wang C. (1993) Aspartyl residue 10 is essential for ATPase activity of rat hsc70. *J Biol Chem.* 268:2063-8.

49. Matta S et al (2012) LRRK2 controls an EndoA phosphorylation cycle in synaptic endocytosis. *Neuron.* 75:1008-21.

50. Shimazu M, Sekito T, Akiyama K, Ohsumi Y, Kakinuma Y. (2005) A family of basic amino acid transporters of the vacuolar membrane from *Saccharomyces cerevisiae. J Biol Chem.* 280:4851-7.

51. Sahu R, Kaushik S, Clement C C, Cannizzo E S, Scharf B, Follenzi A, Potolicchio I, Nieves E, Cuervo A M, Santambrogio L. (2011) Microautophagy of cytosolic proteins by late endosomes. *Dev Cell.* 20:131-9

52. Lee A J, Awano T, Park G H, Monani U R (2012) Limited phenotypic effects of selectively augmenting the SMN protein in the neurons of a mouse model of severe spinal muscular atrophy. *PLoS One.* 7:e46353.

53. Gogliotti R G, Quinlan K A, Barlow C B, Heier C R, Heckman C J, Didonato C J (2012) Motor neuron rescue in spinal muscular atrophy mice demonstrates that sensory-motor defects are a consequence, not a cause, of motor neuron dysfunction. *J Neurosci.* 32:3818-29.

54. Guettier-Sigrist S, Hugel B, Coupin G, Freyssinet J M, Poindron P, Warter J M. (2002) Possible pathogenic role of muscle cell dysfunction in motor neuron death in spinal muscular atrophy. *Muscle Nerve.* 25:700-8.

55. Shafey D, Côté P D, Kothary R (2005) Hypomorphic Smn knockdown C2C12 myoblasts reveal intrinsic defects in myoblast fusion and myotube morphology. *Exp Cell Res.* 311:49-61.

56. Kanisicak O, Mendez J J, Yamamoto S, Yamamoto M, Goldhamer D J. (2009) Progenitors of skeletal muscle satellite cells express the muscle determination gene, MyoD. *Dev Biol.* 332:131-41.

57. Montes, J., McDermott, M. P., Martens, W. B., Dunaway, S., Glanzman, A. M., Riley, S., Quigley, J., Montgomery, M. J., Sproule, D., Tawil, R., Chung, W. K., Darras, B. T., De Vivo, D. C., Kaufmann, P. and Finkel, R. S. (2011) Six-Minute Walk Test demonstrates motor fatigue in spinal muscular atrophy. *Neurology* 74: 833-838

58. Tang M, Gao G, Rueda C B, Yu H, Thibodeaux D N, Awano T, Engelstad K M, Sanchez-Quintero M J, Yang H, Li F, Li H, Su Q, Shetler K E, Jones L, Seo R, McConathy J, Hillman E M, Noebels J L, De Vivo D C, Monani U R (2017) Brain microvasculature defects and Glut1 deficiency syndrome averted by early repletion of the glucose transporter-1 protein. *Nat Commun.* 8:14152.

59. Rudnicki M A, Le Grand F, McKinnell I, Kuang S. (2008) The molecular regulation of muscle stem cell function. *Cold Spring Harb Symp Quant Biol* 10.1101/sqb.2008.73.064

60. Swoboda K J, Prior T W, Scott C B, McNaught T P, Wride M C, Reyna S P, Bromberg M B (2005) Natural history of denervation in SMA: relation to age, SMN2 copy number, and function. *Ann Neurol.* 57:704-12.

61. Lutz C M, Kariya S, Patruni S, Osborne M A, Liu D, Henderson C E, Li D K, Pellizzoni L, Rojas J, Valenzuela D M, Murphy A J, Winberg M L, Monani U R. (2011) Postsymptomatic restoration of SMN rescues the disease phenotype in a mouse model of severe spinal muscular atrophy. *J Clin Invest.* 12:3029-41.

62. Foust K D, Wang X, McGovern V L, Braun L, Bevan A K, Haidet A M, Le T T, Morales P R, Rich M M, Burghes A H, Kaspar B K (2010) Rescue of the spinal muscular atrophy phenotype in a mouse model by early postnatal delivery of SMN. *Nat Biotechnol.* 28:271-4.

63. Hua Y, Sahashi K, Rigo F, Hung G, Horev G, Bennett C F, Krainer A R. (2013) Peripheral SMN restoration is essential for long-term rescue of a severe spinal muscular atrophy mouse model. *Nature* 478: 123-6

64. Hosseinibarkooie S et al (2016) The Power of Human Protective Modifiers: PLS3 and CORO1C Unravel Impaired Endocytosis in Spinal Muscular Atrophy and Rescue SMA Phenotype. *Am J Hum Genet.* 99:647-65.

65. Riessland, M et al (2017) Neurocalcin Delta Suppression Protects against Spinal Muscular Atrophy in Humans and across Species by Restoring Impaired Endocytosis. *Am J Hum Genet.* 100: 297-315

The scope of the present invention is not limited by what has been specifically shown and described hereinabove. Those skilled in the art will recognize that there are suitable alternatives to the depicted examples of materials, configurations, constructions and dimensions. Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety. Variations, modifications and other implementations of what is described herein will occur to those of ordinary skill in the art without departing from the spirit and scope of the invention. While certain embodiments of the present invention have been shown and described, it will be obvious to those skilled in the art that changes and modifications may be made without departing from the spirit and scope of the invention. The matter set forth in the foregoing description and accompanying drawings is offered by way of illustration only and not as a limitation.

What is claimed is:

1. A method of treating a motor neuron disease in a subject, the method comprising administering an effective amount of a nucleic acid molecule encoding a mutant heat shock 70 kDa protein 8 (Hspa8) to the subject, wherein the mutant Hspa8 is Hspa8$^{G470R}$.

2. The method of claim 1, wherein the nucleic acid molecule comprises a recombinant adeno-associated virus (AAV) vector.

3. The method of claim 1, wherein the nucleic acid molecule is administered to the central nervous system (CNS), or to the spinal cord, of the subject.

4. The method of claim 1, wherein the nucleic acid molecule is administered intrathecally, orally, intravenously, intramuscularly, topically, arterially, or subcutaneously.

5. A method of treating a motor neuron disease in a subject, the method comprising administering a modulator of heat shock 70 kDa protein 8 (Hspa8) to the subject, wherein the modulator is a nucleic acid molecule encoding a mutant Hspa8$^{G470R}$.

6. The method of claim 5, wherein the modulator is administered to the central nervous system (CNS), or to the spinal cord, of the subject.

7. The method of claim 1, wherein the motor neuron disease is spinal muscular atrophy (SMA) or amyotrophic lateral sclerosis (ALS).

8. The method of claim 1, wherein the motor neuron disease is hereditary spastic paraplegia (HSP), primary lateral sclerosis (PLS), progressive muscular atrophy (PMA), progressive bulbar palsy (PBP), or pseudobulbar palsy.

9. The method of claim 1, further comprising administering a SMN2 splicing modifier to the subject.

10. The method of claim 1, wherein the subject is a human.

11. The method of claim 5, wherein the motor neuron disease is spinal muscular atrophy (SMA) or amyotrophic lateral sclerosis (ALS).

12. The method of claim 5, wherein the motor neuron disease is hereditary spastic paraplegia (HSP), primary lateral sclerosis (PLS), progressive muscular atrophy (PMA), progressive bulbar palsy (PBP), or pseudobulbar palsy.

13. The method of claim 5, further comprising administering a SMN2 splicing modifier to the subject.

14. The method of claim 5, wherein the subject is a human.

* * * * *